(12) United States Patent
Kolb et al.

(10) Patent No.: US 11,016,108 B2
(45) Date of Patent: *May 25, 2021

(54) MICROFLUIDIC DEVICES AND METHODS FOR PERFORMING SERUM SEPARATION AND BLOOD CROSS-MATCHING

(71) Applicant: PerkinElmer Health Sciences, Inc., Waltham, MA (US)

(72) Inventors: Andrew W. Kolb, Seattle, WA (US); Carolina L. Elmufdi, Bothell, WA (US); C. Frederick Battrell, Wenatchee, WA (US)

(73) Assignee: PERKINELMER HEALTH SCIENCES, INC., Waltham, MA (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/455,454

(22) Filed: Jun. 27, 2019

(65) Prior Publication Data

US 2019/0324045 A1 Oct. 24, 2019

Related U.S. Application Data

(63) Continuation of application No. 14/889,366, filed as application No. PCT/US2014/037192 on May 7, 2014, now Pat. No. 10,386,377.

(Continued)

(51) Int. Cl.
*B01L 3/00* (2006.01)
*G01N 33/80* (2006.01)
*G01N 33/49* (2006.01)

(52) U.S. Cl.
CPC .......... *G01N 33/80* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS 2,770,572 A 11/1956 Eldon
3,013,467 A 12/1961 Marvi
(Continued)

FOREIGN PATENT DOCUMENTS

CN 1146017 A 3/1997
CN 1253625 A 5/2000
(Continued)

OTHER PUBLICATIONS

Al Zahrani et al., "Accuracy and Utility of Commercially Available Amplification and Serologic Tests for the Diagnosis of Minimal Pulmonary Tuberculosis," Am J Respir Crit Care Med 162:1323-1329, 2000.
(Continued)

*Primary Examiner* — Rebecca M Giere
(74) *Attorney, Agent, or Firm* — Seed Intellectual Property Law Group LLP

(57) ABSTRACT

Microfluidic cartridges or devices for serum separation and blood cross-match analysis are provided. The devices may include a serum separation subcircuit alone or in combination with a solute mixing subcircuit. The serum separation subcircuit promotes on-cartridge clotting of a blood sample and manipulates the flow of the separated serum sample for subsequent cross-match analysis with a second blood sample, for example. The solute mixing subcircuit includes at least two intake channels, one for a whole blood sample from, for example, a blood donor and the other for the separated serum sample from, for example, a transfusion recipient. The solute mixing subcircuit further includes a serpentine mixing channel conjoined to a downstream channel. Under vacuum generated by a conjoined finger pump,
(Continued)

the two input streams fill the serpentine mixing and downstream channels due to capillary action, enabling visualization of an agglutination reaction.

16 Claims, 6 Drawing Sheets

Related U.S. Application Data

(60) Provisional application No. 61/820,585, filed on May 7, 2013, provisional application No. 61/820,576, filed on May 7, 2013, provisional application No. 61/820,579, filed on May 7, 2013.

(52) U.S. Cl.
CPC ... *B01L 3/502723* (2013.01); *B01L 3/502738* (2013.01); *B01L 3/502753* (2013.01); *G01N 33/491* (2013.01); *B01L 2200/027* (2013.01); *B01L 2200/10* (2013.01); *B01L 2300/0681* (2013.01); *B01L 2300/0816* (2013.01); *B01L 2300/0883* (2013.01); *B01L 2400/0406* (2013.01); *B01L 2400/0481* (2013.01)

(56) References Cited

U.S. PATENT DOCUMENTS

| | | |
|---|---|---|
| 3,640,267 A | 2/1972 | Hurtig et al. |
| 3,686,355 A | 8/1972 | Gaines, Jr. et al. |
| 3,799,742 A | 3/1974 | Coleman |
| 3,996,345 A | 12/1976 | Ullman et al. |
| 4,104,029 A | 8/1978 | Maier |
| 4,235,960 A | 11/1980 | Sasse et al. |
| 4,304,257 A | 12/1981 | Webster |
| 4,366,241 A | 12/1982 | Tom et al. |
| 4,373,932 A | 2/1983 | Gribnau et al. |
| 4,387,183 A | 6/1983 | Francis |
| 4,477,575 A | 10/1984 | Vogel et al. |
| 4,610,678 A | 9/1986 | Weisman et al. |
| 4,683,195 A | 7/1987 | Mullis et al. |
| 4,683,202 A | 7/1987 | Mullis |
| 4,756,884 A | 7/1988 | Hillman et al. |
| 4,788,729 A | 12/1988 | Walker |
| 4,798,703 A | 1/1989 | Minekane |
| 4,800,159 A | 1/1989 | Mullis et al. |
| 4,810,630 A | 3/1989 | Craig et al. |
| 4,833,332 A | 5/1989 | Robertson, Jr. et al. |
| 4,837,168 A | 6/1989 | De Jaeger et al. |
| 4,848,722 A | 7/1989 | Webster |
| 4,855,240 A | 8/1989 | Rosenstein et al. |
| 4,869,282 A | 9/1989 | Sittler et al. |
| 4,883,750 A | 11/1989 | Whiteley et al. |
| 4,889,818 A | 12/1989 | Gelfand et al. |
| 4,894,416 A | 1/1990 | Gallucci |
| 4,943,522 A | 7/1990 | Eisinger et al. |
| 4,945,039 A | 7/1990 | Suzuki et al. |
| 4,952,516 A | 8/1990 | Matkovich |
| 4,956,302 A | 9/1990 | Gordon et al. |
| 4,965,188 A | 10/1990 | Mullis et al. |
| 5,038,852 A | 8/1991 | Johnson et al. |
| 5,075,078 A | 12/1991 | Osikowicz et al. |
| 5,075,212 A | 12/1991 | Rotbart |
| 5,100,626 A | 3/1992 | Levin |
| 5,120,643 A | 6/1992 | Ching et al. |
| 5,130,238 A | 7/1992 | Malek et al. |
| 5,140,161 A | 8/1992 | Hillman et al. |
| 5,141,850 A | 8/1992 | Cole et al. |
| 5,145,578 A | 9/1992 | Tokubo et al. |
| 5,147,607 A | 9/1992 | Mochida |
| 5,160,701 A | 11/1992 | Brown et al. |
| 5,192,980 A | 3/1993 | Dixon et al. |
| 5,225,163 A | 7/1993 | Andrews |
| 5,231,035 A | 7/1993 | Akers, Jr. |
| 5,234,809 A | 8/1993 | Boom et al. |
| 5,252,459 A | 10/1993 | Tarcha et al. |
| 5,270,183 A | 12/1993 | Corbett et al. |
| 5,273,684 A | 12/1993 | Traber et al. |
| 5,275,785 A | 1/1994 | May et al. |
| 5,296,703 A | 3/1994 | Tsien |
| 5,304,487 A | 4/1994 | Wilding et al. |
| 5,338,689 A | 8/1994 | Yves et al. |
| 5,354,668 A | 10/1994 | Auerbach |
| 5,354,815 A | 10/1994 | Barringer, Jr. et al. |
| 5,387,526 A | 2/1995 | Garner et al. |
| 5,415,994 A | 5/1995 | Imrich et al. |
| 5,420,016 A | 5/1995 | Boguslaski et al. |
| 5,427,930 A | 6/1995 | Birkenmeyer et al. |
| 5,443,890 A | 8/1995 | Ohman |
| 5,447,440 A | 9/1995 | Davis et al. |
| 5,455,166 A | 10/1995 | Walker |
| 5,478,751 A | 12/1995 | Oosta et al. |
| 5,486,335 A | 1/1996 | Wilding et al. |
| 5,489,624 A | 2/1996 | Kantner et al. |
| 5,498,392 A | 3/1996 | Wilding et al. |
| 5,504,013 A | 4/1996 | Senior |
| 5,508,313 A | 4/1996 | Delgado et al. |
| 5,543,026 A | 8/1996 | Hoff et al. |
| 5,552,064 A | 9/1996 | Chachowski et al. |
| 5,565,366 A | 10/1996 | Akers, Jr. |
| 5,578,818 A | 11/1996 | Kain et al. |
| 5,582,989 A | 12/1996 | Caskey et al. |
| 5,587,128 A | 12/1996 | Wilding et al. |
| 5,591,645 A | 1/1997 | Rosenstein |
| 5,593,824 A | 1/1997 | Treml et al. |
| 5,602,040 A | 2/1997 | May et al. |
| 5,614,598 A | 3/1997 | Barringer, Jr. et al. |
| 5,622,871 A | 4/1997 | May et al. |
| 5,631,734 A | 5/1997 | Stern et al. |
| 5,635,358 A | 6/1997 | Wilding et al. |
| 5,635,602 A | 6/1997 | Cantor et al. |
| 5,639,428 A | 6/1997 | Cottingham |
| 5,656,503 A | 8/1997 | May et al. |
| 5,658,723 A | 8/1997 | Oberhardt |
| 5,660,178 A | 8/1997 | Kantner et al. |
| 5,660,370 A | 8/1997 | Webster |
| 5,660,990 A | 8/1997 | Rao et al. |
| 5,670,381 A | 9/1997 | Jou et al. |
| 5,685,758 A | 11/1997 | Paul et al. |
| 5,702,953 A | 12/1997 | Mazurek et al. |
| 5,707,516 A | 1/1998 | Tomizawa et al. |
| 5,707,807 A | 1/1998 | Kato |
| 5,716,842 A | 2/1998 | Baier et al. |
| 5,716,852 A | 2/1998 | Yager et al. |
| 5,718,567 A | 2/1998 | Rapp et al. |
| 5,724,404 A | 3/1998 | Garcia et al. |
| 5,726,026 A | 3/1998 | Wilding et al. |
| 5,726,404 A | 3/1998 | Brody |
| 5,726,751 A | 3/1998 | Altendorf et al. |
| 5,730,850 A | 3/1998 | Kambara et al. |
| 5,731,212 A | 3/1998 | Gavin et al. |
| 5,747,349 A | 5/1998 | Van Denva et al. |
| 5,748,827 A | 5/1998 | Holl et al. |
| 5,759,014 A | 6/1998 | Van Lintel |
| 5,770,460 A | 6/1998 | Pawlak et al. |
| 5,788,927 A | 8/1998 | Farrell et al. |
| 5,795,543 A | 8/1998 | Poto et al. |
| 5,798,273 A | 8/1998 | Shuler et al. |
| 5,830,411 A | 11/1998 | Martinell Gisper-Sauch |
| 5,856,174 A | 1/1999 | Lipshutz et al. |
| 5,863,502 A | 1/1999 | Southgate et al. |
| 5,863,801 A | 1/1999 | Southgate et al. |
| 5,872,710 A | 2/1999 | Kameyama |
| 5,905,028 A | 5/1999 | Frame et al. |
| 5,906,602 A | 5/1999 | Weber et al. |
| 5,922,210 A | 7/1999 | Brody et al. |
| 5,922,591 A | 7/1999 | Anderson et al. |
| 5,928,880 A | 7/1999 | Wilding et al. |
| 5,932,100 A | 8/1999 | Yager et al. |
| 5,932,799 A | 8/1999 | Moles |
| 5,948,684 A | 9/1999 | Weigl et al. |
| 5,955,029 A | 9/1999 | Wilding et al. |
| 5,965,410 A | 10/1999 | Chow et al. |

(56) References Cited

U.S. PATENT DOCUMENTS

| | | |
|---|---|---|
| 5,971,158 A | 10/1999 | Yager et al. |
| 5,971,355 A | 10/1999 | Biegelsen et al. |
| 5,972,710 A | 10/1999 | Weigl et al. |
| 5,972,721 A | 10/1999 | Bruno et al. |
| 5,974,867 A | 11/1999 | Forster et al. |
| 5,985,990 A | 11/1999 | Kantner et al. |
| 5,989,813 A | 11/1999 | Gerdes |
| 6,001,307 A | 12/1999 | Naka et al. |
| 6,007,309 A | 12/1999 | Hartley |
| 6,007,775 A | 12/1999 | Yager |
| 6,018,616 A | 1/2000 | Schaper |
| 6,020,187 A | 2/2000 | Tam |
| 6,037,168 A | 3/2000 | Brown |
| 6,040,048 A | 3/2000 | Kato et al. |
| 6,040,193 A | 3/2000 | Winkler et al. |
| 6,057,167 A | 5/2000 | Shieh et al. |
| 6,068,752 A | 5/2000 | Dubrow et al. |
| 6,086,740 A | 7/2000 | Kennedy |
| 6,114,179 A | 9/2000 | Lapierre et al. |
| 6,121,508 A | 9/2000 | Bischof et al. |
| 6,136,272 A | 10/2000 | Weigl et al. |
| 6,158,712 A | 12/2000 | Craig |
| 6,168,948 B1 | 1/2001 | Anderson et al. |
| 6,171,865 B1 | 1/2001 | Weigl et al. |
| 6,184,029 B1 | 2/2001 | Wilding et al. |
| 6,210,514 B1 | 4/2001 | Cheung et al. |
| 6,210,882 B1 | 4/2001 | Landers et al. |
| 6,239,228 B1 | 5/2001 | Zajaczkowski et al. |
| 6,272,939 B1 | 8/2001 | Frye et al. |
| 6,287,850 B1 | 9/2001 | Besemer et al. |
| 6,297,061 B1 | 10/2001 | Wu et al. |
| 6,303,389 B1 | 10/2001 | Levin et al. |
| 6,309,875 B1 | 10/2001 | Gordon |
| 6,325,975 B1 | 12/2001 | Naka et al. |
| 6,326,211 B1 | 12/2001 | Anderson et al. |
| 6,368,876 B1 | 4/2002 | Huang et al. |
| 6,387,290 B1 | 5/2002 | Brody et al. |
| 6,390,791 B1 | 5/2002 | Maillefer et al. |
| 6,399,398 B1 | 6/2002 | Cunningham et al. |
| 6,409,832 B2 | 6/2002 | Weigl et al. |
| 6,418,968 B1 | 7/2002 | Pezzuto et al. |
| 6,431,212 B1 | 8/2002 | Hayenga et al. |
| 6,432,212 B1 | 8/2002 | Hirose et al. |
| 6,439,036 B1 | 8/2002 | Mansky |
| 6,451,610 B1 | 9/2002 | Gorman et al. |
| 6,468,807 B1 | 10/2002 | Svensson et al. |
| 6,472,161 B1 | 10/2002 | Baugh |
| 6,488,896 B2 | 12/2002 | Weigl et al. |
| 6,506,346 B1 | 1/2003 | Monro |
| 6,541,213 B1 | 4/2003 | Weigl et al. |
| 6,541,274 B2 | 4/2003 | Nagle et al. |
| 6,562,209 B1 | 5/2003 | Sullivan et al. |
| 6,569,674 B1 | 5/2003 | McGarry et al. |
| 6,576,459 B2 | 6/2003 | Miles et al. |
| 6,581,899 B2 | 6/2003 | Williams |
| 6,614,030 B2 | 9/2003 | Maher et al. |
| 6,620,273 B2 | 9/2003 | Dai et al. |
| 6,632,655 B1 | 10/2003 | Mehta et al. |
| 6,635,487 B1 | 10/2003 | Lee et al. |
| 6,637,463 B1 | 10/2003 | Lei et al. |
| 6,664,104 B2 | 12/2003 | Pourahmadi et al. |
| 6,706,836 B1 | 3/2004 | Holguin et al. |
| 6,720,411 B2 | 4/2004 | Mirkin et al. |
| 6,729,352 B2 | 5/2004 | O'Connor et al. |
| 6,731,178 B2 | 5/2004 | Gailhard et al. |
| 6,731,781 B1 | 5/2004 | Shams et al. |
| 6,743,399 B1 | 6/2004 | Weigl et al. |
| 6,748,975 B2 | 6/2004 | Hartshorne et al. |
| 6,752,966 B1 | 6/2004 | Chazan |
| 6,758,107 B2 | 7/2004 | Cabuz |
| 6,767,194 B2 | 7/2004 | Jeon et al. |
| 6,787,338 B2 | 9/2004 | Wittwer et al. |
| 6,793,753 B2 | 9/2004 | Unger et al. |
| 6,815,160 B1 | 11/2004 | Chien et al. |
| 6,843,263 B2 | 1/2005 | Kuo et al. |
| 6,852,284 B1 | 2/2005 | Holl et al. |
| 6,872,566 B2 | 3/2005 | Vischer et al. |
| 6,901,949 B2 | 6/2005 | Cox et al. |
| 6,916,113 B2 | 7/2005 | Van De et al. |
| 6,933,109 B2 | 8/2005 | Anderson |
| 6,951,632 B2 | 10/2005 | Unger et al. |
| 6,953,675 B2 | 10/2005 | Leung et al. |
| 6,953,676 B1 | 10/2005 | Wilding et al. |
| 6,955,738 B2 | 10/2005 | Derand et al. |
| 6,974,119 B2 | 12/2005 | Brendle et al. |
| 6,974,669 B2 | 12/2005 | Mirkin et al. |
| 7,010,391 B2 | 3/2006 | Handique et al. |
| 7,052,594 B2 | 5/2006 | Pelrine et al. |
| 7,087,414 B2 | 8/2006 | Gerdes et al. |
| 7,141,416 B2 | 11/2006 | Krutzik |
| 7,153,673 B2 | 12/2006 | Stern |
| 7,223,363 B2 | 5/2007 | McNeely et al. |
| 7,223,371 B2 | 5/2007 | Hayenga et al. |
| 7,226,562 B2 | 6/2007 | Holl et al. |
| 7,235,400 B2 | 6/2007 | Adey |
| 7,241,421 B2 | 7/2007 | Webster et al. |
| 7,312,085 B2 | 12/2007 | Chou et al. |
| 7,318,913 B2 | 1/2008 | Loeffler et al. |
| 7,378,451 B2 | 5/2008 | Levitt et al. |
| 7,416,892 B2 | 8/2008 | Battrell et al. |
| 7,419,638 B2 | 9/2008 | Saltsman et al. |
| 7,445,926 B2 | 11/2008 | Mathies et al. |
| 7,467,928 B2 | 12/2008 | Fakunle et al. |
| 7,514,212 B2 | 4/2009 | Prudent et al. |
| 7,517,651 B2 | 4/2009 | Marshall et al. |
| 7,541,147 B2 | 6/2009 | Marshall et al. |
| 7,544,506 B2 | 6/2009 | Breidford et al. |
| 7,607,641 B1 | 10/2009 | Yuan |
| 7,615,370 B2 | 11/2009 | Streit et al. |
| 7,618,590 B2 | 11/2009 | Gleason et al. |
| 7,648,835 B2 | 1/2010 | Breidford et al. |
| 7,695,683 B2 | 4/2010 | Quan et al. |
| 7,749,444 B2 | 7/2010 | Yamada et al. |
| 7,763,453 B2 | 7/2010 | Clemmens et al. |
| 7,785,776 B2 | 8/2010 | Wittwer et al. |
| 7,832,429 B2 | 11/2010 | Young et al. |
| 7,906,317 B2 | 3/2011 | Lee et al. |
| 7,955,836 B2 | 6/2011 | Clemmens et al. |
| 8,104,497 B2 | 1/2012 | Unger et al. |
| 8,104,514 B2 | 1/2012 | Fernandes et al. |
| 8,110,392 B2 | 2/2012 | Battrell et al. |
| 8,222,023 B2 | 7/2012 | Battrell et al. |
| 8,318,109 B2 | 11/2012 | Saltsman et al. |
| 8,318,439 B2 | 11/2012 | Battrell et al. |
| 8,329,453 B2 | 12/2012 | Battrell et al. |
| 8,431,389 B2 | 4/2013 | Battrell et al. |
| 8,557,198 B2 | 10/2013 | Saltsman et al. |
| 8,697,009 B2 | 4/2014 | Saltsman et al. |
| 8,716,007 B2 | 5/2014 | Battrell et al. |
| 8,747,779 B2 | 6/2014 | Sprague et al. |
| 8,772,017 B2 | 7/2014 | Battrell et al. |
| 9,056,291 B2 | 6/2015 | Battrell et al. |
| 9,132,423 B2 | 9/2015 | Battrell et al. |
| 9,146,246 B2 | 9/2015 | Battrell et al. |
| 9,272,280 B2 | 3/2016 | Viola et al. |
| 10,087,440 B2 | 10/2018 | Lofquist et al. |
| 10,107,797 B2 | 10/2018 | Battrell et al. |
| 2001/0027745 A1 | 10/2001 | Weigl et al. |
| 2001/0046701 A1 | 11/2001 | Schulte et al. |
| 2002/0022261 A1 | 2/2002 | Anderson et al. |
| 2002/0037499 A1 | 3/2002 | Quake et al. |
| 2002/0081569 A1 | 6/2002 | Anderson |
| 2002/0081934 A1 | 6/2002 | Murao et al. |
| 2002/0086443 A1 | 7/2002 | Bamdad |
| 2002/0137196 A1 | 9/2002 | Miles et al. |
| 2002/0148992 A1 | 10/2002 | Hayenga et al. |
| 2002/0155010 A1 | 10/2002 | Karp et al. |
| 2002/0160518 A1 | 10/2002 | Hayenga et al. |
| 2002/0164816 A1 | 11/2002 | Quake |
| 2002/0192676 A1 | 12/2002 | Madonna et al. |
| 2002/0195152 A1 | 12/2002 | Fernandes et al. |
| 2003/0008308 A1 | 1/2003 | Enzelberger et al. |
| 2003/0013184 A1 | 1/2003 | Streit et al. |
| 2003/0013203 A1 | 1/2003 | Jedrzejewski et al. |

(56) References Cited

U.S. PATENT DOCUMENTS

| | | |
|---|---|---|
| 2003/0032028 A1 | 2/2003 | Dace et al. |
| 2003/0073229 A1 | 4/2003 | Greenstein et al. |
| 2003/0124619 A1 | 7/2003 | Weigl et al. |
| 2003/0124623 A1 | 7/2003 | Yager et al. |
| 2003/0129756 A1 | 7/2003 | Thorne et al. |
| 2003/0136178 A1 | 7/2003 | Cabuz |
| 2003/0152927 A1 | 8/2003 | Jakobsen et al. |
| 2003/0152994 A1 | 8/2003 | Woudenberg et al. |
| 2003/0153686 A1 | 8/2003 | Onoe et al. |
| 2003/0175990 A1 | 9/2003 | Hayenga et al. |
| 2003/0185713 A1 | 10/2003 | Leonard et al. |
| 2003/0215818 A1 | 11/2003 | Lorenz |
| 2003/0215825 A1 | 11/2003 | Tong |
| 2003/0224434 A1 | 12/2003 | Wittwer et al. |
| 2004/0005718 A1 | 1/2004 | Fukushima |
| 2004/0018611 A1 | 1/2004 | Ward et al. |
| 2004/0024051 A1 | 2/2004 | Holton |
| 2004/0037739 A1 | 2/2004 | McNeely et al. |
| 2004/0065930 A1 | 4/2004 | Lin et al. |
| 2004/0081997 A1 | 4/2004 | Stern |
| 2004/0115094 A1 | 6/2004 | Gumbrecht et al. |
| 2004/0115831 A1 | 6/2004 | Meathrel et al. |
| 2004/0115838 A1 | 6/2004 | Quake et al. |
| 2004/0121364 A1 | 6/2004 | Chee et al. |
| 2004/0124384 A1 | 7/2004 | Biegelsen et al. |
| 2004/0129678 A1 | 7/2004 | Crowley et al. |
| 2004/0189311 A1 | 9/2004 | Glezer et al. |
| 2004/0209354 A1 | 10/2004 | Mathies et al. |
| 2004/0224339 A1 | 11/2004 | Numajiri et al. |
| 2004/0224425 A1 | 11/2004 | Gjerde et al. |
| 2004/0226348 A1 | 11/2004 | Bruce et al. |
| 2004/0241051 A1 | 12/2004 | Wyzgol et al. |
| 2004/0242770 A1 | 12/2004 | Feldstein et al. |
| 2004/0248167 A1 | 12/2004 | Quake et al. |
| 2004/0265171 A1 | 12/2004 | Pugia et al. |
| 2005/0013732 A1 | 1/2005 | Battrell et al. |
| 2005/0019792 A1 | 1/2005 | McBride et al. |
| 2005/0019898 A1 | 1/2005 | Adey et al. |
| 2005/0037397 A1 | 2/2005 | Mirkin et al. |
| 2005/0041525 A1 | 2/2005 | Pugia et al. |
| 2005/0084421 A1 | 4/2005 | Unger et al. |
| 2005/0106066 A1 | 5/2005 | Saltsman et al. |
| 2005/0106742 A1 | 5/2005 | Wahl et al. |
| 2005/0118570 A1 | 6/2005 | Hollis et al. |
| 2005/0129581 A1 | 6/2005 | McBride et al. |
| 2005/0129582 A1 | 6/2005 | Breidford et al. |
| 2005/0136552 A1 | 6/2005 | Buechler |
| 2005/0142582 A1 | 6/2005 | Doyle et al. |
| 2005/0157301 A1 | 7/2005 | Chediak et al. |
| 2005/0161669 A1 | 7/2005 | Jovanovich et al. |
| 2005/0164373 A1 | 7/2005 | Oldham et al. |
| 2005/0186585 A1 | 8/2005 | Juncosa et al. |
| 2005/0205816 A1 | 9/2005 | Hayenga et al. |
| 2005/0217741 A1 | 10/2005 | Bohm |
| 2005/0221281 A1 | 10/2005 | Ho |
| 2005/0284817 A1 | 12/2005 | Fernandez et al. |
| 2006/0003440 A1 | 1/2006 | Streit et al. |
| 2006/0073484 A1 | 4/2006 | Mathies et al. |
| 2006/0076068 A1 | 4/2006 | Young et al. |
| 2006/0094119 A1 | 5/2006 | Ismagilov et al. |
| 2006/0099116 A1 | 5/2006 | Manger et al. |
| 2006/0099413 A1 | 5/2006 | Lu |
| 2006/0105402 A1 | 5/2006 | Rott et al. |
| 2006/0127886 A1 | 6/2006 | Kaylor et al. |
| 2006/0166375 A1 | 7/2006 | Hawkins et al. |
| 2006/0178568 A1 | 8/2006 | Danna et al. |
| 2006/0245978 A1 | 11/2006 | Prins |
| 2006/0246575 A1 | 11/2006 | Lancaster et al. |
| 2006/0254916 A1 | 11/2006 | Hernandez et al. |
| 2006/0263816 A1 | 11/2006 | Laikhter et al. |
| 2006/0264782 A1 | 11/2006 | Holmes et al. |
| 2006/0275852 A1 | 12/2006 | Montagu et al. |
| 2006/0275893 A1 | 12/2006 | Ishii et al. |
| 2006/0292588 A1 | 12/2006 | Chou et al. |
| 2006/0292630 A1 | 12/2006 | Fukumoto |
| 2007/0003447 A1 | 1/2007 | Gleason et al. |
| 2007/0008536 A1 | 1/2007 | Mitani et al. |
| 2007/0009383 A1 | 1/2007 | Bedingham et al. |
| 2007/0014695 A1 | 1/2007 | Yue et al. |
| 2007/0042427 A1 | 2/2007 | Gerdes et al. |
| 2007/0077610 A1 | 4/2007 | Ghai et al. |
| 2007/0125947 A1 | 6/2007 | Sprinzak et al. |
| 2007/0134810 A1 | 6/2007 | Yang et al. |
| 2007/0154895 A1 | 7/2007 | Spaid et al. |
| 2007/0166199 A1 | 7/2007 | Zhou et al. |
| 2007/0183935 A1 | 8/2007 | Clemmens et al. |
| 2007/0190525 A1 | 8/2007 | Gu et al. |
| 2007/0219366 A1 | 9/2007 | Gumbrecht et al. |
| 2007/0234785 A1 | 10/2007 | Beerling et al. |
| 2007/0243603 A1 | 10/2007 | Einsle et al. |
| 2007/0248983 A1 | 10/2007 | Schwind et al. |
| 2007/0280856 A1 | 12/2007 | Ulmanella et al. |
| 2007/0292858 A1 | 12/2007 | Chen et al. |
| 2008/0050283 A1 | 2/2008 | Chou et al. |
| 2008/0056953 A1 | 3/2008 | Yamada et al. |
| 2008/0081341 A1 | 4/2008 | Maher et al. |
| 2008/0085551 A1 | 4/2008 | Kim et al. |
| 2008/0124749 A1 | 5/2008 | Farnam et al. |
| 2008/0145280 A1 | 6/2008 | Bookbinder et al. |
| 2008/0226500 A1 | 9/2008 | Shikida et al. |
| 2008/0260586 A1 | 10/2008 | Boamfa |
| 2008/0274511 A1 | 11/2008 | Tan et al. |
| 2008/0297792 A1 | 12/2008 | Kim et al. |
| 2009/0000678 A1 | 1/2009 | Therriault et al. |
| 2009/0017483 A1 | 1/2009 | Yamaoka et al. |
| 2009/0022624 A1 | 1/2009 | Saltsman et al. |
| 2009/0047713 A1 | 2/2009 | Handique |
| 2009/0061450 A1 | 3/2009 | Hunter |
| 2009/0111159 A1 | 4/2009 | Brolaski et al. |
| 2009/0148847 A1 | 6/2009 | Kokoris et al. |
| 2009/0148933 A1 | 6/2009 | Battrell et al. |
| 2009/0181411 A1 | 7/2009 | Battrell et al. |
| 2009/0298059 A1 | 12/2009 | Gumbrecht et al. |
| 2009/0325203 A1 | 12/2009 | Jenny et al. |
| 2009/0325276 A1 | 12/2009 | Battrell et al. |
| 2010/0041049 A1 | 2/2010 | Smith et al. |
| 2010/0112723 A1 | 5/2010 | Battrell et al. |
| 2010/0120129 A1 | 5/2010 | Amshey et al. |
| 2010/0167384 A1 | 7/2010 | Clemmens et al. |
| 2010/0173395 A1 | 7/2010 | Saltsman et al. |
| 2010/0291588 A1 | 11/2010 | McDevitt et al. |
| 2010/0303687 A1 | 12/2010 | Blaga et al. |
| 2011/0151479 A1 | 6/2011 | Stevens et al. |
| 2011/0207621 A1 | 8/2011 | Montagu et al. |
| 2012/0028342 A1 | 2/2012 | Ismagilov et al. |
| 2012/0064597 A1 | 3/2012 | Clemmens et al. |
| 2012/0071342 A1 | 3/2012 | Lochhead et al. |
| 2012/0115214 A1 | 5/2012 | Battrell et al. |
| 2012/0135511 A1 | 5/2012 | Battrell et al. |
| 2012/0156750 A1 | 6/2012 | Battrell et al. |
| 2012/0164383 A1 | 6/2012 | Sollmann |
| 2012/0164627 A1 | 6/2012 | Battrell et al. |
| 2012/0177543 A1 | 7/2012 | Battrell et al. |
| 2012/0329142 A1 | 12/2012 | Battrell et al. |
| 2013/0011912 A1 | 1/2013 | Battrell et al. |
| 2013/0017552 A1 | 1/2013 | Rudorfer |
| 2013/0032235 A1 | 2/2013 | Johnstone et al. |
| 2013/0130262 A1 | 5/2013 | Battrell et al. |
| 2013/0142708 A1 | 6/2013 | Battrell et al. |
| 2014/0349381 A1 | 11/2014 | Battrell et al. |
| 2014/0370581 A1 | 12/2014 | Saltsman et al. |
| 2015/0158026 A1 | 6/2015 | Battrell et al. |
| 2015/0321193 A1 | 11/2015 | Sprague et al. |
| 2015/0346097 A1 | 12/2015 | Battrell et al. |
| 2015/0352549 A1 | 12/2015 | Kolb et al. |
| 2016/0102340 A1 | 4/2016 | Bouzek |
| 2016/0109467 A1 | 4/2016 | Kolb et al. |
| 2016/0209431 A1 | 7/2016 | Battrell et al. |
| 2017/0113221 A1 | 4/2017 | Hoffman et al. |

FOREIGN PATENT DOCUMENTS

| | | |
|---|---|---|
| CN | 102602087 A | 7/2012 |
| DE | 20 2004 012 163 U1 | 11/2004 |

(56) References Cited

FOREIGN PATENT DOCUMENTS

| | | |
|---|---|---|
| EP | 0 039 195 B1 | 6/1986 |
| EP | 0 320 308 A2 | 6/1989 |
| EP | 0 329 822 A2 | 8/1989 |
| EP | 0 399 859 A1 | 11/1990 |
| EP | 0 456 699 B1 | 11/1991 |
| EP | 0 517 631 A1 | 12/1992 |
| EP | 6-94722 A | 4/1994 |
| EP | 7-151101 A | 6/1995 |
| EP | 0 869 979 B1 | 11/2000 |
| EP | 1 203 959 A1 | 5/2002 |
| EP | 1 240 945 A2 | 9/2002 |
| EP | 1 180 135 B1 | 8/2005 |
| EP | 1 659 405 A1 | 5/2006 |
| EP | 1 707 965 A1 | 10/2006 |
| EP | 1 726 940 A1 | 11/2006 |
| EP | 1 792 654 A2 | 6/2007 |
| EP | 1 263 533 B1 | 3/2010 |
| EP | 2 202 328 A1 | 6/2010 |
| GB | 2 202 328 A | 9/1988 |
| JP | 52-55679 A | 5/1977 |
| JP | 61-137066 A | 6/1986 |
| JP | 7-056258 A | 7/1995 |
| JP | 7-506430 A | 7/1995 |
| JP | 7-506431 A | 7/1995 |
| JP | 2520468 Y2 | 12/1996 |
| JP | 9-509498 A | 9/1997 |
| JP | 10-82773 A | 3/1998 |
| JP | 10-132712 A | 5/1998 |
| JP | 10-504916 A | 5/1998 |
| JP | 11-508182 A | 7/1999 |
| JP | 11-508347 a | 7/1999 |
| JP | 11-509094 A | 8/1999 |
| JP | 11-512645 A | 11/1999 |
| JP | 2000-314719 A | 11/2000 |
| JP | 2002-17861 A | 1/2002 |
| JP | 2002-371955 A | 12/2002 |
| JP | 2003-166910 A | 6/2003 |
| JP | 2003-207454 A | 7/2003 |
| JP | 2003-220897 A | 8/2003 |
| JP | 2004-028589 A | 1/2004 |
| JP | 2004-333452 A | 11/2004 |
| JP | 2005-512071 A | 4/2005 |
| JP | 2005-527303 A | 9/2005 |
| JP | 2005-531006 A | 10/2005 |
| JP | 2005-345378 A | 12/2005 |
| JP | 2006-73371 A | 3/2006 |
| JP | 2006-84459 A | 3/2006 |
| JP | 2006-90774 A | 4/2006 |
| JP | 2006-512092 A | 4/2006 |
| JP | 2006-122743 A | 5/2006 |
| JP | 2006-517029 A | 7/2006 |
| JP | 2006-227301 A | 8/2006 |
| JP | 2006-246777 A | 9/2006 |
| JP | 2006-520190 A | 9/2006 |
| JP | 2007-514142 A | 5/2007 |
| JP | 2007-532918 A | 11/2007 |
| JP | 2008-503722 A | 2/2008 |
| JP | 2008-89597 A | 4/2008 |
| JP | 2008-96375 A | 4/2008 |
| JP | 2008-537063 A | 9/2008 |
| JP | 2009-14529 A | 1/2009 |
| JP | 2009-019962 A | 1/2009 |
| JP | 2009-510337 A | 3/2009 |
| JP | 2009-513966 A | 4/2009 |
| JP | 2009-529883 A | 8/2009 |
| JP | 2009-255083 A | 11/2009 |
| JP | 2010-78508 A | 4/2010 |
| JP | 2010-519463 A | 6/2010 |
| JP | 2010-535346 A | 11/2010 |
| JP | 2012-516455 A | 7/2012 |
| JP | 2013-518289 A | 5/2013 |
| JP | 2015-510111 A | 4/2015 |
| JP | 2016-508197 A | 3/2016 |
| TW | 590982 B | 6/2004 |
| WO | 86/06488 A1 | 11/1986 |
| WO | 88/08534 A1 | 11/1988 |
| WO | 88/10315 A1 | 12/1988 |
| WO | 89/06700 A1 | 7/1989 |
| WO | 89/09284 A1 | 10/1989 |
| WO | 90/09596 A1 | 8/1990 |
| WO | 91/12336 A1 | 8/1991 |
| WO | 93/25889 A1 | 12/1993 |
| WO | 96/14934 A1 | 5/1996 |
| WO | 96/33399 A1 | 10/1996 |
| WO | 97/01055 A1 | 1/1997 |
| WO | 97/02357 A1 | 1/1997 |
| WO | 97/39338 A1 | 10/1997 |
| WO | 97/47390 A1 | 12/1997 |
| WO | 97/48779 A1 | 12/1997 |
| WO | 98/49543 A1 | 11/1998 |
| WO | 99/17100 A1 | 4/1999 |
| WO | 99/22858 A1 | 5/1999 |
| WO | 00/22436 A1 | 4/2000 |
| WO | 00/56828 A1 | 9/2000 |
| WO | 00/63670 A1 | 10/2000 |
| WO | 01/10565 A1 | 2/2001 |
| WO | 01/13127 A1 | 2/2001 |
| WO | 01/26813 A2 | 4/2001 |
| WO | 01/68238 A2 | 9/2001 |
| WO | 01/070381 A1 | 9/2001 |
| WO | 01/75415 A2 | 10/2001 |
| WO | 02/001184 A1 | 1/2002 |
| WO | 02/012896 A1 | 2/2002 |
| WO | 02/041994 A2 | 5/2002 |
| WO | 02/072262 A1 | 9/2002 |
| WO | 02/081934 A2 | 10/2002 |
| WO | 03/007786 A2 | 1/2003 |
| WO | 03/015923 A1 | 2/2003 |
| WO | 03/031977 A2 | 4/2003 |
| WO | 03/049860 A1 | 6/2003 |
| WO | 03/054523 A2 | 7/2003 |
| WO | 03/097831 A1 | 11/2003 |
| WO | 03/099355 A2 | 12/2003 |
| WO | 03/101887 A2 | 12/2003 |
| WO | 03/102546 A2 | 12/2003 |
| WO | 2004/055198 A2 | 7/2004 |
| WO | 2004/061085 A2 | 7/2004 |
| WO | 2004/065010 A2 | 8/2004 |
| WO | 2004/065930 A2 | 8/2004 |
| WO | 2004/093786 A2 | 11/2004 |
| WO | 2005/016529 A1 | 2/2005 |
| WO | 2005/022154 A1 | 3/2005 |
| WO | 2005/066638 A1 | 7/2005 |
| WO | 2005/069015 A1 | 7/2005 |
| WO | 2005/083025 A1 | 9/2005 |
| WO | 2005/088280 A1 | 9/2005 |
| WO | 2005/090970 A1 | 9/2005 |
| WO | 2005/106024 A2 | 11/2005 |
| WO | 2005/118849 A1 | 12/2005 |
| WO | 2006/009724 A2 | 1/2006 |
| WO | 2006/018811 A1 | 2/2006 |
| WO | 2006/035830 A1 | 4/2006 |
| WO | 2006/052652 A2 | 5/2006 |
| WO | 2006/076567 A2 | 7/2006 |
| WO | 2006/083833 A2 | 8/2006 |
| WO | 2006/125767 A1 | 11/2006 |
| WO | 2007/049009 A1 | 5/2007 |
| WO | 2007/064635 A1 | 6/2007 |
| WO | 2007/106579 A2 | 9/2007 |
| WO | 2007/106580 A2 | 9/2007 |
| WO | 2007/109584 A1 | 9/2007 |
| WO | 2007/137291 A1 | 11/2007 |
| WO | 2008/002462 A2 | 1/2008 |
| WO | 2008/036544 A1 | 3/2008 |
| WO | 2008/070198 A2 | 6/2008 |
| WO | 2008/101732 A1 | 8/2008 |
| WO | 2008/147382 A1 | 12/2008 |
| WO | 2009/018473 A1 | 2/2009 |
| WO | 2009/037361 A1 | 3/2009 |
| WO | 2009/105711 A1 | 8/2009 |
| WO | 2010/025302 A2 | 3/2010 |
| WO | 2010/040103 A1 | 4/2010 |
| WO | 2010/088514 A1 | 8/2010 |
| WO | 2011/094577 A2 | 8/2011 |

(56) References Cited

FOREIGN PATENT DOCUMENTS

| WO | 2012/071069 A1 | 5/2012 |
|---|---|---|
| WO | 2013/010674 A1 | 1/2013 |
| WO | 2013/052318 A1 | 4/2013 |
| WO | 2014/100732 A1 | 6/2014 |
| WO | 2014/182831 A1 | 11/2014 |
| WO | 2014/182844 A1 | 11/2014 |
| WO | 2014/182847 A1 | 11/2014 |

OTHER PUBLICATIONS

Aoki et al., "Serine Repeat Antigen (SERA5) Is Predominantly Expressed among the SERA Multigene Family of Plasmodium falciparum, and the Acquired Antibody Titers Correlate with Serum Inhibition of the Parasite Growth," The Journal of Biological Chemistry 277(49):47533-47540, 2002.
Arar et al., "Synthesis and Antiviral Activity of Peptide-Oligonucleotide Conjugates Prepared by Using Nα-(Bromoacetyl)peptides," Bioconjugate Chem. 6(5):573-577, 1995.
Arikan et al., "Anti-Kp 90 IgA Antibodies in the Diagnosis of Active Tuberculosis," CHEST 114(5):1253-1257, 1998.
Bangs Laboratories, Inc., "Lateral Flow Tests," TechNote 303, Rev. #002, Apr. 11, 2008. (7 pages).
Birkelund, "The molecular biology and diagnostics of Chlamydia trachomatis," Danish Medical Bulletin 39(4):304-320, Aug. 1992.
Bongartz et al., "Improved biological activity of antisense oligonucleotides conjugated to a fusogenic peptide," Nucleic Acids Research 22(22):4681-4688, 1994.
Bowden et al., "Using Self-Administered Tampons to Diagnose STDs," AIDS Patient Care and STDs 12(1):29-32, 1998.
C. Fredrick Battrell et al., "Sample-To-Answer Microfluidic Cartridge," U.S. Appl. No. 14/819,182, filed Aug. 5, 2015, 78 pages.
Cady, "Quantum Dot Molecular Beacons for DNA Detection," in Micro and Nano Technologies in Bioanalysis, Lee et al., (eds.), Humana Press, 2009, pp. 367-379.
Cai et al., "Interactions of DNA with Clay Minerals and Soil Colloidal Particles and Protection against Degradation by Dnase," Environ. Sci. Technol. 40:2971-2976, 2006.
Carmona et al., "The use of Fluorescence Resonance Energy Transfer (FRET) peptides for measurement of clinically important proteolytic enzymes," An Acad Bras Cienc 81(3):381-392, 2009.
Chan et al., "Polymer surface modification by plasmas and photons," Surface Science Reports 24:1-54, 1996.
Chernesky et al., "Clinical Evaluation of the Sensitivity and Specificity of a Commercially Available Enzyme Immunoassay for Detection of Rubella Virus-Specific Immunoglobulin M," J. Clin. Microbiol. 20(3):400-404, 1984.
Chernesky et al., "Detection of Chlamydia trachomatis Antigens by Enzyme Immunoassay and Immunofluorescence in Genital Specimens from Symptomatic and Asymptomatic Men and Women," The Journal of Infectious Diseases 154(1):141-148, 1986.
Chou et al., "Prevention of pre-PCR mis-priming and primer dimerization improves low-copy-number-amplifications," Nucleic Acids Research 20(7):1717-1723, 1992.
Cissell et al., "Resonance energy transfer methods of RNA detection," Anal. Bioanal. Chem. 393:125-135, 2008.
Coombs et al., "A New Test for the Detection of Weak and "Incomplete" RH Agglutinins," *Brit J Exp Path* 26:255-266, Jul. 1945.
Crotchfelt et al., "Detection of Neisseria gonorrhoeae and Chlamydia trachomatis in Genitourinary Specimens from Men and Women by a Coamplification PCR Assay," J. Clin. Microbiol. 35(6):1536-1540, 1997.
Cuzzubbo et al., "Use of Recombinant Envelope Proteins for Serological Diagnosis of Dengue Virus Infection in an Immunochromatographic Assay," Clin. Diagn. Lab. Immunol. 8(6):1150-1155, 2001.

D'Aquila et al., "Maximizing sensitivity and specificity of PCR by pre-amplification heating," Nucleic Acids Research 19(13):3749, 1991.
Dean et al., "Comprehensive human genome amplification using multiple displacement amplification," PNAS 99(8):5261-5266, 2002.
Detter et al., "Isothermal Strand-Displacement Amplification Applications for High-Throughput Genomics," Genomics 80(6):691-698, 2002.
Dujardin et al., "Errors in Interpreting the Pretransfusion Bedside Compatibility Test," *Vox Sang* 78:37-43, 2000.
Edelstein et al., "The BARC biosensor applied to the detection of biological warfare agents," Biosensors & Bioelectronics 14:805-813, 2000.
Egger et al., "Reverse Transcription Multiplex PCR for Differentiation between Polio- and Enteroviruses from Clinical and Environmental Samples," Journal of Clinical Microbiology 33(6):1442-1447, 1995.
Eritja et al., "Synthesis of Defined Peptide-Oligonucleotide Hybrids Containing a Nuclear Transport Signal Sequence," Tetrahedron 47(24):4113-4120, 1991.
Fontana et al., "Performance of Strand Displacement Amplification Assay in the Detection of Chlamydia trachomatis and Neisseria gonorrhoeae," Jpn. J. Infect. Dis. 58:283-288, 2005.
Frame et al., "Identification and Typing of Herpes Simplex Virus by Enzyme Immunoassay with Monoclonal Antibodies," J. Clin. Microbiol. 20(2):162-166, 1984.
Franchi et al., "Cations as Mediators of the Adsorption of Nucleic Acids on Clay Surfaces in Prebiotic Environments," Orgins of Life and Evolution of the Biosphere 33:1-16, 2003.
Freund et al., (eds.), "Film buckling, bulging, and peeling," in Thin Film Materials: Stress, Defect Formation and Surface Evolution, Cambridge, UK, The University of Cambridge, 2003, pp. 312-386. (77 pages).
Frohman, "Race: Rapid Amplification of cDNA Ends," in PCR Protocols: A Guide to Methods and Applications, Innis et al., (eds.), New York , Academic Press, Inc., 1990, pp. 28-38.
Gallo et al., "Study of viral integration of HPV-16 in young patients with LSIL," J. Clin. Pathol. 56:532-536, 2003.
Garbassi et al., "Chapter 6: Physical Modifications," in Polymer Surfaces-From Physics to Technology, John Wiley and Sons, Baltimore, Md., 1994, pp. 223-241.
Genovese et al., "Virus Variability and Its Impact on HIV and Hepatitis Therapy," Advances in Virology 2012:607527, 2012. (3 pages).
Ghai et al., "Identification, expression, and functional characterization of MAEBL, a sporozoite and asexual blood stage chimeric erythrocyte-binding protein of Plasmodium falciparum," Molecular & Biochemical Parasitology 123:35-45, 2002.
Gijs, "Magnetic bead handling on-chip: new opportunities for analytical applications," Microfluid Nanofluid 1:22-40, 2004.
Gomes et al., "Immunoreactivity and differential developmental expression of known and putative Chlamydia trachomatis membrane proteins for biologically variant serovars representing distinct disease groups," Microbes and Infection 7:410-420, 2005.
Graham et al., "Magnetoresistive-based biosensors and biochips," TRENDS in Biotechnology 22(9):455-462, 2004.
Graves et al., "Development of Antibody to Measles Virus Polypeptides During Complicated and Uncomplicated Measles Virus Infections," Journal of Virology 49(2):409-412, 1984.
Gravesen et al., "Microfluidics—a review," *J. Micromech. Microeng.* 3:168-182, 1993.
Grover et al., "Monolithic membrane valves and diaphragm pumps for practical large-scale integration into glass microfluidic devices," Sensors and Actuators B 89:315-323, 2003.
Hardt et al., "Passive micromixers for applications in the microreactor and µTAS fields," Microfluid Nanofluid 1:108-118, 2005.
Harris et al., "Typing of Dengue Viruses in Clinical Specimens and Mosquitoes by Single-Tube Multiplex Reverse Transcriptase PCR," J. Clin. Microbiol. 36(9):2634-2639, 1998.
Harrison et al., "Synthesis and hybridization analysis of a small library of peptide-oligonucleotide conjugates," Nucleic Acids Research 26(13):3136-3145, 1998.

(56) References Cited

OTHER PUBLICATIONS

Hatch et al., "A rapid diffusion immunoassay in a T-sensor," *Nature Biotechnology* 19:461-465, May 2001.
Hosokawa et al., "Hydrophobic Microcapillary Vent for Pneumatic Manipulation of Liquid in mTas," Proceedings of the uTAS '98 Workshop, held in Banff, Canada, 307-310, Oct. 13-16, 1998, 6 pages.
Huft et al., "Fabrication of High-Quality Microfluidic Solid-Phase Chromatography Columns," Anal. Chem. 85:1797-1802, 2013.
Hummel et al., "Development of quantitative gene-specific real-time RT-PCR assays for the detection of measles virus in clinical specimens," Journal of Virological Methods 132:166-173, 2006.
Hung et al., "A specificity enhancer for polymerase chain reaction," Nucleic Acids Research. 18(16):4953, 1990.
Ingrand et al., "Reliability of the pretransfusion bedside compatibility test: association with transfusion practice and training," *Transfusion* 38:1030-1036, Nov./Dec. 1998.
Innis et al., (eds.), "Optimization of PCRs," in PCR Protocols: A Guide to Methods and Applications, Academic Press, Inc., San Diego, California, 1990, pp. 3-12. (11 pages).
Jacobs et al., "Detection of *Streptococcus pneumoniae* Antigen in Bronchoalveolar Lavage Fluid Samples by a Rapid Immunochromatographic Membrane Assay," J. Clin. Microbiol. 43(8):4037-4040, 2005.
Joung et al., "Micropumps Based on Alternating High-Gradient Magnetic Fields," IEEE Transactions on Magnetics 36(4):2012-2014, 2000.
Kanehisa, "Use of statistical criteria for screening potential homologies in nucleic acid sequences," Nucleic Acids Research 12(1):203-213, 1984.
Kellogg et al., "TaqStart Antibody™: 'Hot Start' PCR Facilitated by a Neutralizing Monoclonal Antibody Directed Against Taq DNA Polymerase," BioTechniques 16(6):1134-1137, 1994. (6 pages).
Kennedy et al., "Protein-Protein Coupling Reactions and the Applications of Protein Conjugates," Clinica Chimica Acta 70:1-31, 1976. (16 pages).
Khan et al., "Antibiotic Resistance, Virulence Gene, and Molecular Profiles of Shiga Toxin-Producing *Escherichia coli* Isolates from Diverse Sources in Calcutta, India," J. Clin. Microbiol. 40(6):2009-2015, 2002.
Khan et al., "Prevalence and Genetic Profiling of Virulence Determinants of Non-O157 Shiga Toxin-Producing *Escherichia coli* Isolated from Cattle, Beef, and Humans, Calcutta, India," Emerging Infectious Diseases 8(1):54-62, 2002.
Khanna et al., "Transformation of Bacillus subtilis by DNA Bound on Montmorillonite and Effect of DNase on the Transforming Ability of Bound DNA," Applied and Environmental Microbiology 58(6):1930-1939, 1992.
Kittigul et al., "Use of a Rapid Immunochromatographic Test for Early Diagnosis of Dengue Virus Infection," Eur. J. Clin. Microbiol. Infect. Dis. 21:224-226, 2002.
Knox et al., "Evaluation of Self-Collected Samples in Contrast to Practitioner-Collected Samples for Detection of Chlamydia trachomatis, Neisseria gonorrhoeae, and Trichomonas vaginalis by Polymerase Chain Reaction Among Women Living in Remote Areas," Sexually Transmitted Diseases 29(11):647-654, 2002.
Krasnoperov et al., "Luminescent Probes for Ultrasensitive Detection of Nucleic Acids," Bioconjug. Chem. 21(2):319-327, 2010. (20 pages).
Kremer et al., "Measles Virus Genotyping by Nucleotide-Specific Multiplex PCR," J. Clin. Microbiol. 42(7):3017-3022, 2004.
Kuipers et al., "Detection of Chlamydia trachomatis in peripheral blood leukocytes of reactive arthritis patients by polymerase chain reaction," Arthritis & Rheumatism 41(10):1894-1895, 1998.
Kuipers et al., "Sensitivities of PCR, MicroTrak, ChlamydiaEIA, IDEIA, and PACE 2 for Purified Chlamydia trachomatis Elementary Bodies in Urine, Peripheral Blood, Peripheral Blood Leukocytes, and Synovial Fluid," J. Clin. Microbiol. 33(12):3186-3190, 1995.
Kuno, "Universal diagnostic RT-PCR protocol for arboviruses," Journal of Virological Methods 72:27-41, 1998.
Kwoh et al., "Transcription-based amplification system and detection of amplified human immunodeficiency virus type 1 with a bead-based sandwich hybridization format," Proc. Natl. Acad. Sci. U.S.A. 86:1173-1177, 1989.
Lage et al., "Whole Genome Analysis of Genetic Alterations in Small DNA Samples Using Hyperbranched Strand Displacement Amplification and Array-CGH," Genome Research 13:294-307, 2003.
Lanciotti et al., "Rapid Detection and Typing of Dengue Viruses from Clinical Samples by Using Reverse Transcriptase-Polymerase Chain Reaction," J. Clin. Microbiol. 30(3):545-551, 1992.
Lapierre et al., "The gel test: a new way to detect red cell antigen-antibody reactions," *Transfusion* 30(2):109-113, 1990.
Leclerc et al., "Meager genetic variability of the human malaria agent Plasmodium vivax," PNAS 101(40):14455-14460, 2004.
Lee et al., "Flow Characteristics of Hydrophilic/Hydrophobic Capillaries Considering Surface Tension," 2nd Annual International IEEE-EMBS Special Topic Conference on Microtechnologies in Medicine & Biology, Poster 150, 560-564, May 2-4, 2002.
Lee et al., "Implementation of Force Differentiation in the Immunoassay," Analytical Biochemistry 287:261-271, 2000.
Leung et al., "Rapid antigen detection testing in diagnosing group A β-hemolytic *Streptococcal pharyngitis*," Expert. Rev. Mol. Diagn. 6(5):761-766, 2006.
Li et al., "Molecular beacons: An optimal multifunctional biological probe," Biochemical and Biophysical Research Communications 373:457-461, 2008.
Lindegren et al., "Optimized Diagnosis of Acute Dengue Fever in Swedish Travelers by a Combination of Reverse Transcription-PCR and Immunoglobulin M Detection," J. Clin. Microbiol. 43(6):2850-2855, 2005.
Ling et al., "The Plasmodium falciparum clag9 gene encodes a rhoptry protein that is transferred to the host erythrocyte upon invasion," Molecular Microbiology 52(1):107-118, 2004.
Lundquist et al., "Human Recombinant Antibodies against Plasmodium falciparum Merozoite Surface Protein 3 Cloned from Peripheral Blood Leukocytes of Individuals with Immunity to Malaria Demonstrate Antiparasitic Properties," Infect. Immun. 74(6):3222-3231, 2006.
Luxton et al., "Use of External Magnetic Fields to Reduce Reaction Times in an Immunoassay Using Micrometer-Sized Paramagnetic Particles as Labels (Magnetoimmunoassay)," Anal. Chem. 76(6):1715-1719, 2004.
Mahony et al., "Chlamydia trachomatis confirmatory testing of PCR-positive genitourinary specimens using a second set of plasmid primers," Molecular and Cellular Probes 6:381-388, 1992.
Mahony et al., "Comparison of Plasmid- and Chromosome-Based Polymerase Chain Reaction Assays for Detecting Chlamydia trachomatis Nucleic Acids," J. Clin. Microbiol. 31(7):1753-1758, 1993.
Mahony et al., "Detection of Antichlamydial Immunoglobulin G and M Antibodies by Enzyme-Linked Immunosorbent Assay," J. Clin. Microbiol. 18(2):270-275, 1983.
Mahony et al., "Multiplex PCR for Detection of Chlamydia trachomatis and Neisseria gonorrhoeae in Genitourinary Specimens," J. Clin. Microbiol. 33(11):3049-3053, 1995.
Mahony, "Multiplex Polymerase Chain Reaction for the Diagnosis of Sexually Transmitted Diseases," Clinics in Laboratory Medicine 16(1):61-71, 1996.
Mayta et al., "Use of a reliable PCR assay for the detection of Neisseria gonorrhoeae in Peruvian patients," Clinical Microbiology and Infection 12(8):809-812, 2006.
Michon et al., "Naturally Acquired and Vaccine-Elicited Antibodies Block Erythrocyte Cytoadherence of the Plasmodium vivax Duffy Binding Protein," Infect. Immun. 68(6):3164-3171, 2000.
Migeot et al., "Reliability of bedside ABO testing before transfusion," *Transfusion* 42:1348-1355, Oct. 2002.
Migot-Nabias et al., "Immune Responses Against Plasmodium Falciparum Asexual Blood-Stage Antigens and Disease Susceptibility in Gabonese and Cameroonian Children," Am. J. Trop. Med. Hyg. 61(3):488-494, 1999.
Mitrani-Rosenbaum et al., "Simultaneous detection of three common sexually transmitted agents by polymerase chain reaction," Am J Obstet Gynecol 171(3):784-790, 1994.

(56) References Cited

OTHER PUBLICATIONS

Mohmmed et al., "Identification of karyopherin β as an immunogenic antigen of the malaria parasite using immune mice and human sera," Parasite Immunology 27:197-203, 2005.

Monis et al., "Nucleic acid amplification-based techniques for pathogen detection and identification," Infection, Genetics and Evolution 6:2-12, 2006.

Morré et al., "RNA Amplification by Nucleic Acid Sequence-Based Amplification with an Internal Standard Enables Reliable Detection of Chlamydia trachomatis in Cervical Scrapings and Urine Samples," J. Clin. Microbiol. 34(12):3108-3114, 1996.

Narum et al., "A novel Plasmodium falciparum erythrocyte binding protein-2 (EBP2/BAEBL) involved in erythrocyte receptor binding," Molecular & Biochemical Parasitology 119:159-168, 2002.

NCBI Database, GenBank Accession No. ACOL01000910, Jun. 9, 2009. (2 pages).

NCBI Database, GenBank Accession No. ACOL01004315, Jun. 9, 2009. (2 pages).

NCBI Database, GenBank Accession No. ACOL01004318, Jun. 9, 2009. (1 page).

NCBI Database, GenBank Accession No. ACOL01004329, Jun. 9, 2009. (1 page).

NCBI Database, GenBank Accession No. ACOL01004331, Jun. 9, 2009. (1 page).

NCBI Database, GenBank Accession No. NP_473155, Jan. 3, 2007. (2 pages).

Nielsen et al., "Detection of Immunoglobulin G Antibodies to Cytomegalovirus Antigens by Antibody Capture Enzyme-Linked Immunosorbent Assay," J. Clin. Microbiol. 24(6):998-1003, 1986.

Notomi et al., "Loop-mediated isothermal amplification of DNA," Nucleic Acids Research 28(12):e63, 2000. (7 pages).

Oeuvray et al., "Merozoite Surface Protein-3: A Malaria Protein Inducing Antibodies that Promote Plasmodium falciparum Killing by Cooperation With Blood Monocytes," Blood 84(5):1594-1602, 1994.

Ohara et al., "One-sided polymerase chain reaction: The amplification of cDNA," Proc. Natl. Acad. Sci. U.S.A. 86:5673-5677, 1989.

Ohta et al., "Enzyme-Linked Immunosorbent Assay of Influenza Specific IgA Antibody in Nasal Mucus," Acta Paediatr. Jpn. 33:617-622, 1991. (8 pages).

Østergaard et al., "A novel approach to the automation of clinical chemistry by controlled manipulation of magnetic particles," Journal of Magnetism and Magnetic Materials 194:156-162, 1999.

Ozoemena et al., "Comparative Evaluation of Measles Virus Specific TaqMan PCR and Conventional PCR Using Synthetic and Natural RNA Templates," Journal of Medical Virology 73:79-84, 2004.

Park et al., "Polymorphisms of p53, p21 and IRF-1 and cervical cancer susceptibility in Korean women," Proceedings of the American Association of Cancer Research 44, Second Edition, p. 1081, 2003.

Pfyffer et al., "Diagnostic Performance of Amplified Mycobacterium tuberculosis Direct Test with Cerebrospinal Fluid, Other Nonrespiratory, and Respiratory Specimens," Journal of Clinical Microbiology 34(4):834-841, 1996.

Pinder et al., "Immunoglobulin G Antibodies to Merozoite Surface Antigens Are Associated with Recovery from Choroquine-Resistant Plasmodium falciparum in Gambian Children," Infect. Immun. 74(5):2887-2893, 2006.

Pingle et al., "Multiplexed Identification of Blood-Borne Bacterial Pathogens by Use of a Novel 16S rRNA Gene PCR-Ligase Detection Reaction-Capillary Electrophoresis Assay," J. Clin. Microbiol. 45(6):1927-1935, 2007.

Polley et al., "Vaccination for vivax malaria: targeting the invaders," TRENDS in Parasitology 20(3):99-102, 2004.

Polpanich et al., "Detection of Malaria Infection via Latex Agglutination Assay," *Anal. Chem.* 79:4690-4695, 2007.

Porstmann et al., "Comparison of Chromogens for the Determination of Horseradish Peroxidase as a Marker in Enzyme Immunoassay," J. Clin. Chem. Clin. Biochem. 19(7):435-439, 1981.

Ramachandran et al., "Dry-reagent storage for disposable lab-on-a-card diagnosis of enteric pathogens," Proceedings of the 1st Distributed Diagnosis and Home Healthcare (D2H2) Conference, Arlington, Virginia, USA, Apr. 2-4, 2006, pp. 16-19.

Ranjan et al., "Mapping regions containing binding residues within functional domains of Plasmodium vivax and Plasmodium knowlesi erythrocyte-binding proteins," PNAS 96(24):14067-14072, 1999.

Rida et al., "Long-range transport of magnetic microbeads using simple planar coils placed in a uniform magnetostatic field," Applied Physics Letters 83(12):2396-2398, 2003.

Roosendaal et al., "Comparison of different primer sets for detection of Chlamydia trachomatis by the polymerase chain reaction," J. Med. Microbiol. 38:426-433, 1993.

Schachter et al., "Ligase Chain Reaction to Detect Chlamydia trachomatis Infection of the Cervix," J. Clin. Microbiol. 32(10):2540-2543, 1994.

Shi et al., "Fabrication and optimization of the multiplex PCR-based oligonucleotide microarray for detection of Neisseria gonorrhoeae, Chlamydia trachomatis and Ureaplasma urealyticum," Journal of Microbiological Methods 62:245-256, 2005.

Shi et al., "Natural Immune Response to the C-Terminal 19-Kilodalton Domain of Plasmodium falciparum Merozoite Surface Protein 1," Infect. Immun. 64(7):2716-2723, 1996.

Shu et al., "Development of Group- and Serotype-Specific One-Step SYBR Green I-Based Real-Time Reverse Transcription-PCR Assay for Dengue Virus," J. Clin. Microbiol. 41(6):2408-2416, 2003.

Snounou et al., "High sensitivity of detection of human malaria parasites by the use of nested polymerase chain reaction," Molecular and Biochemical Parasitology 61:315-320, 1993.

Soukchareun et al., "Use of Nα-Fmoc-cysteine(S-thiobutyl) Derivatized Oligodeoxynucleotides for the Preparation of Oligodeoxynucleotide—Peptide Hybrid Molecules," Bioconjugate Chem. 9:466-475, 1998.

Staben et al., "Particle transport in Poiseuille flow in narrow channels," International Journal of Multiphase Flow 31:529-547, 2005.

Stetsenko et al., "Efficient Conjugation of Peptides to Oligonucleotides by 'Native Ligation'," J. Org. Chem. 65:4900-4908, 2000.

Sturm et al., "Vaginal tampons as specimen collection device for the molecular diagnosis of non-ulcerative sexually transmitted infections in antenatal clinic attendees," International Journal of STD & AIDS 15:94-98, 2004.

Tai et al., "Artificial Receptors in Serologic Tests for the Early Diagnosis of Dengue Virus Infection," Clinical Chemistry 52(8):1486-1491, 2006.

Tamim et al., "Cervicovaginal coinfections with human papillomavirus and chlamydia trachomatis," Diagnostic Microbiology and Infectious Disease 43:277-281, 2002.

Thompson et al., "Kinetics and proposed mechanism of the reaction of an immunoinhibition, particle-enhanced immunoassay," *Clinical Chemistry* 43(11):2384-2389, 1997.

Tongren et al., "Target Antigen, Age, and Duration of Antigen Exposure Independently Regulate Immunoglobulin G Subclass Switching in Malaria," Infect. Immun. 74(1):257-264, 2006.

Trenholme et al., "Antibody Reactivity to Linear Epitopes of Plasmodium Falciparum Cytoadherence-Linked Asexual Gene 9 in Asymptomatic Children and Adults From Papua New Guinea," Am. J. Trop. Med. Hyg. 72(6):708-713, 2005.

Tung et al., "Preparation and Applications of Peptide—Oligonucleotide Conjugates," Bioconjugate Chem. 11(5):605-618, 2000.

Tung et al., "Preparation of Oligonucleotide-Peptide Conjugates," Bioconjugate Chem. 2:464-465, 1991. (4 pages).

Unger et al., "Monolithic Microfabricated Valves and Pumps by Multilayer Soft Lithography," Science 288:113-116, 2000. (5 pages).

van Gemen et al., "Quantification of HIV-1 RNA in plasma using NASBA™ during HIV-1 primary infection," Journal of Virological Methods 43:177-188, 1993. (14 pages).

Van Lintel, "A Piezoelectric Micropump Based on Micromachining of Silicon," Sensors and Actuators 15:153-167, 1988.

(56) References Cited

OTHER PUBLICATIONS

Vinayagamoorthy et al., "Nucleotide Sequence-Based Multitarget Identification," J. Clin. Microbiol. 41(7):3284-3292, 2003.

Vives et al., "Selective Coupling of a Highly Basic Peptide to an Oligonucleotide," Tetrahedron Letters 38(7):1183-1186, 1997. (7 pages).

Walker et al., "Strand displacement amplification—an isothermal, in vitro DNA amplification technique," Nucleic Acids Research 20(7):1691-1696, 1992. (8 pages).

Walker, "Empirical Aspects of Strand Displacement Amplification," PCR Methods and Applications 3:1-6, 1993.

Wang et al., "Molecular Engineering of DNA: Molecular Beacons," Angew Chem Int Ed Engl 48(5):856-870, 2009. (34 pages).

Watson et al., Molecular Biology of the Gene, 4th Ed., Benjamin Cummings Publishing Company, Menlo Park, California, Jan. 1987, pp. 226-227. (4 pages).

Weigl et al., "Fully integrated multiplexed lab-on-a-card assay for enteric pathogens," Proc. of SPIE 6112:611202, 2006. (11 pages).

Weinstock et al., "Sexually Transmitted Diseases Among American Youth: Incidence and Prevalence Estimates, 2000," Perspectives on Sexual and Reproductive Heath 36(1):6-10, 2004.

Whiley et al., "Comparison of three in-house multiplex PCR assays for the detection of Neisseria gonorrhoeae and Chlamydia trachomatis using real-time and conventional detection methodologies," Pathology 37(5):364-370, 2005.

Witkin et al., "Detection of Chlamydia trachomatis by the polymerase chain reaction in the cervices of women with acute salpingitis," Am. J. Obstet. Gynecol. 168(5):1438-1442, 1993.

Woehlbier et al., "Analysis of Antibodies Directed against Merozoite Surface Protein 1 of the Human Malaria Parasite Plasmodium falciparum," Infect. Immun. 74(2):1313-1322, 2006.

Wu et al., "The Ligation Amplification Reaction (LAR)—Amplification of Specific DNA Sequences Using Sequential Rounds of Template-Dependent Ligation," Genomics 4(1):560-569, 1989. (11 pages).

Yogi et al., "Clinical Evaluation of the Bladder Tumor Marker 'TU-MARK-BTA'," Hinyokika Kiyo 37(4):335-339, 1991.

Zhang et al., "Synthesis of clay minerals," Applied Clay Science 50:1-11, 2010.

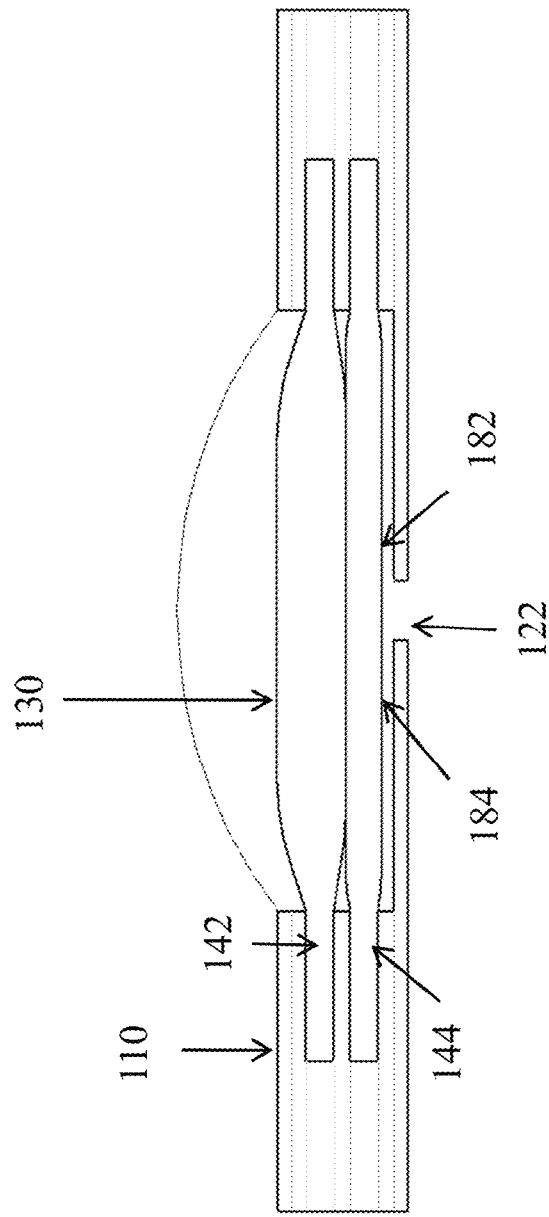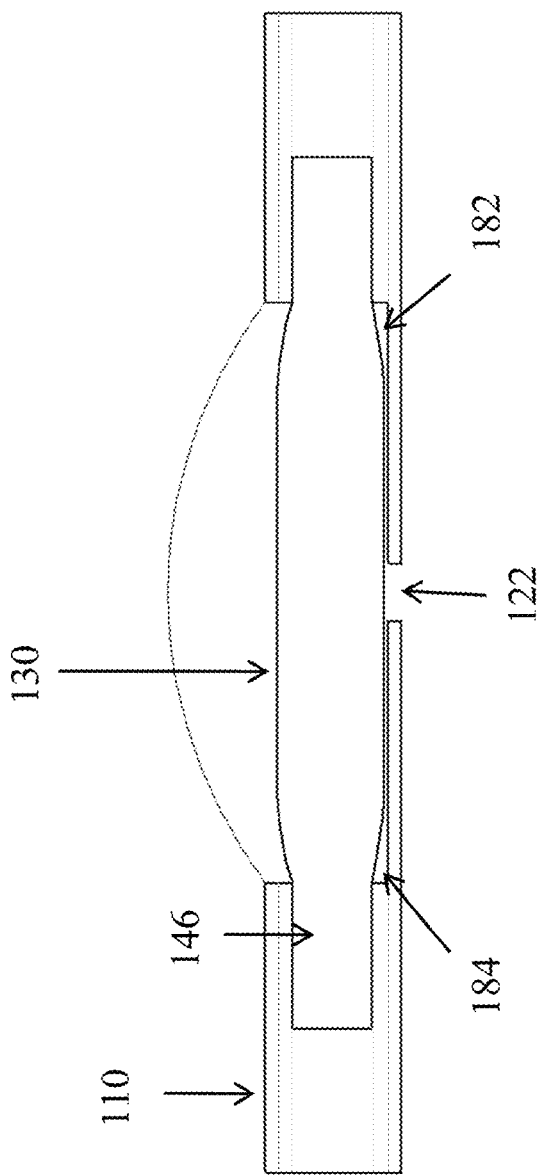
FIG. 2A
FIG. 2B

MICROFLUIDIC DEVICES AND METHODS FOR PERFORMING SERUM SEPARATION AND BLOOD CROSS-MATCHING

BACKGROUND

Technical Field

This invention generally pertains to devices, apparatus, and methods for separation of serum from whole blood and potentiation of agglutination reactions in microfluidic devices. Agglutination reactions involving antigen:antibody reactions are useful in cross-matching for blood transfusion.

Description of the Related Art

Analysis of blood prior to transfusion or for clinical assessments relies on diagnostic devices, such as cross-matching or blood-typing devices, and blood chemistry monitors that measure metabolites such as glucose or cholesterol. Such devices must frequently use serum, the uncolored fluid portion of the blood containing analytes of interest to clinicians. Serum samples are separated from whole blood before analysis to remove red blood cells and clotting factors, which have the potential to interfere with cross-match agglutination reactions, colorimetric tests, as well as contribute to hematocrit-dependent variations amongst samples. Therefore, prior to testing, a preprocessing operation is required in which the blood sample is separated into a serum and a clot containing red blood cells.

In the conventional method of serum separation, a whole blood sample is placed in a blood collection tube, allowed to clot, and subjected to centrifugal separation, which enables collection of the serum fraction. However, there has been a dramatic transition in diagnostic analysis from the macroscale to the microscale, with specimen volume requirements decreasing from milliliters to microliters, thereby reducing assay times from hours to minutes. The conventional method of serum separation, requiring sample centrifugation, is obviously not amenable to microscale adaptation. As the engineering of microfluidic diagnostic devices continues to be the focus of competitive research, there is a neglected need for improvements in the preparation of samples for analysis. In adapting these devices for clinical diagnosis, special features are needed to provide serum separated from red blood cells and clotting factors.

Administration of blood in the form of packed erythrocytes or whole blood is often critical in the treatment of trauma, hypovolemic shock, anemia and clotting disorders. Blood transfusion typically requires characterization of the donor blood so as to match the ABO blood type of the donor and recipient, or, more generally, requires a cross-match analysis. This is done to avoid a hemolytic transfusion reaction in which red cells having a major incompatibility antigen are inadvertently administered to a recipient having an antibody to that antigen, and also to avoid the minor side reaction in which a red cell antigen in the recipient's blood is attacked by antibodies in the plasma of the donor. Serious consequences such as kidney failure or splenic rupture can result from a transfusion of mismatched blood.

Currently, medical technicians in the field do not have access to a simple and accurate means of evaluating a donor and recipient pair for possible transfusion reactions during emergency medical treatment, for example, during military operations. Tube agglutination assays are currently used prior to blood transfusion, however these assays are cumbersome and involve erythrocyte preparation and long incubation times. These assays may not always lead to consistent results depending upon the experience of the technician. Additionally, some technicians do not have access to a laboratory qualified to perform agglutination assays. Therefore, there is a strong need in the art for a blood cross-matching device that is quick and simple to use and thus amenable for evaluation of donor and recipient transfusion compatibility during emergency medical care. The present invention fulfills these needs and provides further related advantages.

BRIEF SUMMARY

In one aspect, the present invention provides a microfluidic device having utility in any number of applications, such as for separating a serum fraction from a whole blood sample. In one embodiment, the microfluidic device includes: a) a microfluidic channel having a first end and a second end; b) a sample inlet fluidly connected to the first end of the microfluidic channel configured for receiving a blood sample; and c) a composite membrane interposed between the sample inlet and the first end of the microfluidic channel, wherein the composite membrane is capable of activating blood coagulation and removing selected particles from the blood; and d) an optional on-device pump fluidly connected to the second end of the microfluidic channel. In certain embodiments the optional on-device pump is present. In another embodiment, the composite membrane of the microfluidic device includes at least two membranes. In another embodiment, the composite membrane includes a glass fiber filter. In another embodiment, the composite membrane includes a glass fiber filter and a porous membrane. In another embodiment, the composite membrane also includes an activator of blood coagulation.

In another aspect, the present invention provides microfluidic cartridges and devices which may be used for a number of different assays, including for cross-match assessment of a blood donor and a blood recipient. In one embodiment, the microfluidic cartridge or device includes: a) a fluid separation subcircuit that includes: i) a microfluidic channel having a first end and a second end; ii) a sample inlet fluidly connected to the first end of the microfluidic channel configured for receiving a blood sample; iii) a composite membrane interposed between the sample inlet and the first end of the microfluidic channel, wherein the composite membrane is capable of activating blood coagulation and removing selected particles from the blood; and iv) an optional on-device pump fluidly connected to the second end of the microfluidic channel; and b) a solute mixing subcircuit that includes: i) a serpentine mixing channel, said mixing channel having a first end and a second end and having a critical length for enabling solute mixture by diffusion; ii) a first and second intake channel fluidly joined to said first end of said mixing channel at a staging union; said first intake channel for conveying a first fluid and said second channel for conveying a second fluid; wherein said staging union is configured with a micro-passive valve for simultaneously releasing said first and second fluids into said mixing channel; iii) a downstream channel fluidly joined to the second end of said mixing channel, wherein the downstream channel has a width greater than the width of the mixing channel; iv) a pump for controlledly initiating fluid flow across said micro-passive valve, wherein said pump is fluidly connected to said downstream channel, and initiates flow by a suction stroke; and v) a vent terminating said downstream channel. In certain embodiments the optional on-device pump is present. In another embodiment, the microfluidic cartridge further includes a third intake channel fluidly joined to the first end of the mixing channel at the staging union; the third intake channel for conveying a third fluid to said staging area. In yet another embodiment of the microfluidic cartridge, the fluid separation subcircuit and solute mixing subcircuits are fluidly connected. In another embodiment of the invention, the composite membrane includes at least two membranes. In another embodiment of the invention, the composite membrane includes a glass filter. In another embodiment of the invention, the composite membrane includes a glass filter and a porous membrane. In another embodiment of the invention, the composite membrane includes an activator of blood coagulation.

Methods for using the microfluidic devices for separation of serum from blood samples and for cross-matching donor and recipient samples are also provided.

BRIEF DESCRIPTION OF THE DRAWINGS

FIGS. 2A-B are cross-sectional views illustrating the operation of a second and third embodiment of a microfluidic device in accordance with aspects of the present invention.

DETAILED DESCRIPTION

Figure 1:
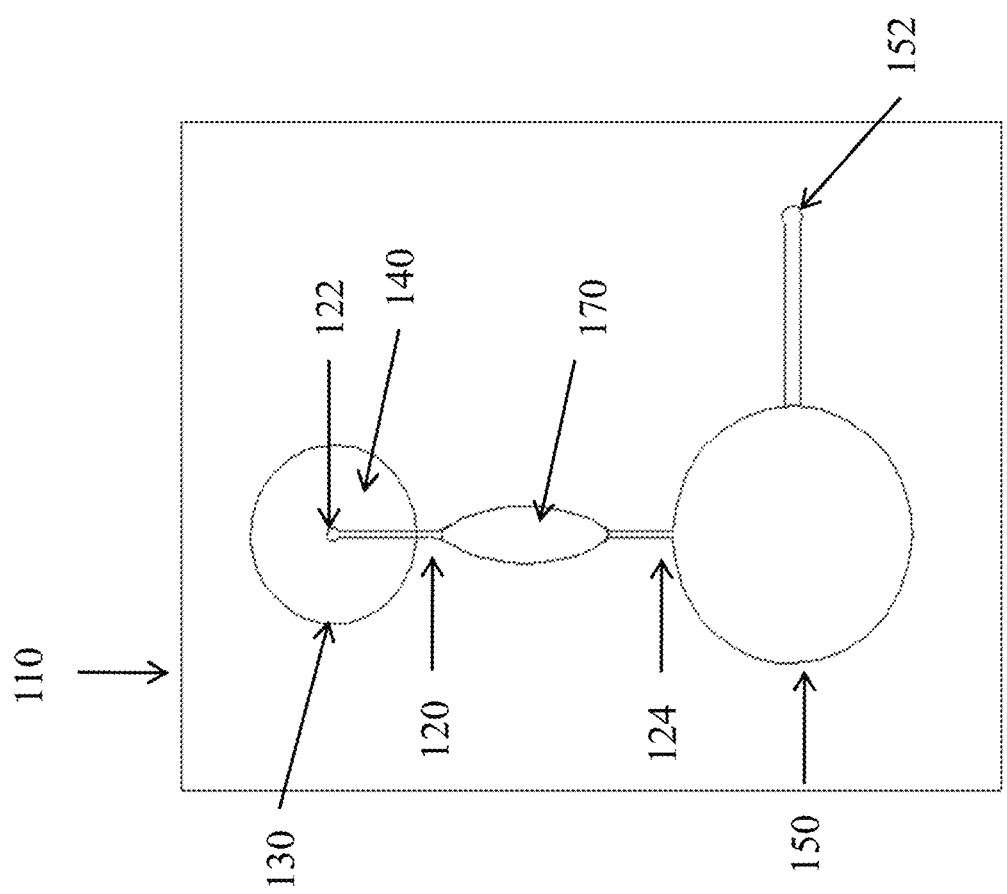
FIG. 1 is a schematic view illustrating the operation of a first embodiment of a microfluidic device in accordance with aspects of the present invention.

In one aspect, the present invention provides a microfluidic device configured to prepare a serum sample for analysis and methods for use of the same. The device is capable of promoting blood coagulation and manipulating the flow of the fluid sample in order to prepare a separated serum sample. The device employs a composite membrane that is capable of providing a matrix to hold a blood sample in place while promoting coagulation. Various embodiments of the device further utilize a plurality of microfluidic channels, inlets, valves, pumps, and other elements arranged in various configurations.

In another aspect, the present invention provides microfluidic cartridges and devices configured to conduct cross-match assessments of blood samples from a donor and a recipient and methods for use of the same. Whole blood from the intended recipient is initially applied to a fluid subcircuit that comprises a composite filter designed to promote on-cartridge coagulation and particle separation, thereby providing an isolated serum sample for cross-match assessment. Packed red cells or whole blood from a donor unit and the separated serum from the intended recipient are added to separate intake channels of the mixing subcircuit of the microfluidic cartridge of the present invention. The donor and recipient samples are contacted in a side-by-side diffusion interface created in a serpentine channel of the mixing subcircuit. Diffusion of solutes between samples in the mixing channel leads to immune binding and visible agglutination reactions if the donor and recipient blood types are not compatible. A downstream flow control channel, with a dimension greater than that of the serpentine mixing channel, modulates and prolongs the liquid flow rate, thereby potentiating immune binding and agglutination reactions. In reactions run for up to ten minutes, agglutination due to incompatibility between blood donor and recipient was easily visually detectable using the microfluidic cartridges of the present invention. If no agglutination was observed, then the blood donor and the recipient are compatible.

1. Definitions

These definitions are provided as an aid in interpreting the claims and specification herein. Where works are cited by reference, and definitions contained therein are inconsistent with those supplied here, the definition used therein shall apply only to the work cited and not to this disclosure.

Microfluidic cartridge: a "device", "card", or "chip" with internal fluid-handling mesostructures by convention having at least one dimension less than 500 µm. These fluidic structures may include microfluidic channels, chambers, valves, vents, vias, pumps, inlets, nipples, and detection means, for example.

Microfluidic channel: as used here, is an enclosed conduit or passage for a fluid having a z-dimension of less than 500 µm, more preferably less than or about 250 µm, and most preferably about or less than 100 µm (about 4 mils), and a cross-sectional area that is broader than deep. The most narrow dimension, also termed the "critical dimension", of a channel has the most profound effect on flow, Reynolds Number, pressure drop, and in the devices described here, the most narrow dimension is typically the z-dimension or diameter.

Microfluidic channels with generally rectangular cross-sections are characterized by x-, y- and z-dimensions. The x-dimension is taken as the length "L" of the channel along the axis of flow, the y-dimension as the width and the z-dimension as the depth. When formed by injection molding, the channel roof and walls are typically joined by a radius. Some microfluidic channels have a circular cross-section and are characterized by a diameter. Other shapes are also possible.

It will be recognized that the words "top", "bottom", "upper", "lower", "side", "roof", "floor", "base" and "horizontal" as used here are relative terms and do not necessarily describe the orientation of the device or device components in relation to the plane of the earth's surface unless explicitly stated to be so. The use of the devices flat on the surface of a table is not intended to be limiting and the z-axis is generally chosen to be perpendicular to the major plane of the device body only as a matter of convenience in explanation and manufacture.

Finger (Bellows) Pump: is a device formed as a cavity, often cylindrical in shape, covered by a flexible, distensible diaphragm, and with an upstream microfluidic channel inlet and a downstream outlet fluidly connected to the cavity. In operation, by placing a vent as the outlet, the diaphragm can be pressed down without generating a differential pressure in the cavity, but by then covering the vent and releasing the elastic diaphragm, a suction pressure pulse is generated that finds use in drawing fluid through the inlet microfluidic channel. In the devices of the present invention, a suction pulse of this kind serves to initiate the assay by initiating fluid flow through a capillary stop; the suction pulse, however, is not required or desired for sustaining fluid flow, which is driven by passive flow capillarity once the upstream microfluidic channel is wetted.

Surfactants: are amphiphilic molecules that lower the surface and interfacial tensions of a liquid by collecting at the surface, allowing easier spreading on a solid surface and reducing the contact angle. Anionic, cationic, zwitterionic, nonionic, and fluorophilic surfactants are contemplated. Anionic surfactants include sodium dioctyl sulfosuccinate (e.g., Aerosol OT-75) marketed by CYTEC Industries. Non-ionic surfactants include polysorbates (e.g., polysorbate 80), polyoxyethylene lauryl ether, n-lauryl-ß-D-maltopyranoside (LM), cetyl ether, stearyl ether, and nonylphenyl ether, Tween® 80, Triton® X-100, and other surfactants. As nonionic surfactants, polyoxyethylene alkyl ether, polyoxyethylene alkyl phenyl ether, polyoxyethylene-polyoxypropylene condensate, acyl polyoxyethylene sorbitan ester, alkyl polyoxyethylene ether, n-dodecyl-ß-D-maltoside, sucrose monolaurate, polyoxyethylene lauryl ether, polyoxyethylene alkylene phenyl ether, polyoxyethylene alkylene tribenzyl phenyl ether, polyoxyethylene glycol p-t-octyl phenyl ether, polyoxyethylene higher alcohol ether, polyoxyethylene fatty acid ester, polyoxyethylene sorbitan fatty acid ester, sorbitan fatty acid ester, polyoxyethylene sorbitol fatty acid ester, polyoxyethylene alkylamine, glycerol fatty acid ester, n-octyl-ß-D-thioglucoside, cetyl ether (C16), lauryl ether (C12), oleyl ether, behenyl ether (C20), polyoxyethylene monolaurate and the like are used. Commercially available nonionic surfactants of this type include Igepal® CO-610 marketed by the GAF Corporation; and Triton® CF-12, X-45, X-114, X-100 and X-102, all marketed by the Dow Chemical Company; Tergitol®15-S-9 marketed by the Union Carbide Corporation; PLURAFAC® RA-40 marketed by BASF Corp; Neodol® 23-6.5 marketed by the Shell Chemical Company and Kyro EOB marketed by the Procter & Gamble Company. Amphoteric or zwitterionic surfactants are also useful in providing detergency, emulsification, wetting and conditioning properties. Representative amphoteric surfactants include fatty acid amides of amino acids (such as Amisoft® LS-11 and HS-21 made by Ajinomoto), N-coco-3-aminopropionic acid and acid salts, N-tallow-3-iminodiproprionate salts. As well as N-lauryl-3-iminodiproprionate disodium salt, N-carboxymethyl-N-cocoalkyl-N-dimethylammonium hydroxide, N-carboxymethyl-N-dimethyl-N-(9-octadecenyl)ammonium hydroxide, (1-carboxyheptadecyl)-trimethylammonium hydroxide, (1-carboxyundecyl) trimethylammonium hydroxide, N-cocoamidoethyl-N-hydroxyethylglycine sodium salt, N-hydroxyethyl-N-stearamidoglycine sodium salt, N-hydroxyethyl-N-lauramido-ß-alanine sodium salt, N-cocoamido-N-hydroxyethyl-ß-alanine sodium salt, as well as mixed alicyclic amines, and their ethoxylated and sulfated sodium salts, 2-alkyl-1-carboxymethyl-1-hydroxyethyl-2-imidazolinium hydroxide sodium salt or free acid wherein the alkyl group may be nonyl, undecyl, or heptadecyl. Also useful are 1,1-bis(carboxymethyl)-2-undecyl-2-imidazolinium hydroxide disodium salt and oleic acid-ethylenediamine condensate, propoxylated and sulfated sodium salt. Amine oxide amphoteric surfactants are also useful. This list is by no means exclusive or limiting.

Surfactants can be added to a reagent to modify the surface tension of the reagent or added to a solid substrate to modify the interfacial tension of the substrate. During molding of a plastic article with a surfactant additive, a sufficient number of surfactant molecules migrate to the surface of the substrate, a process called "blooming", so as to yield a low contact angle surface. The process is described in US Patent Application 2008/0145280 to Bookbinder, which is incorporated herein by reference in its entirety.

Surfactants useful as admixtures with plastics to provide hydrophilic surface properties include polyethylene oxide, polypropylene oxide, nonylphenol ethyoxylate and polyalkylenyeneoxide modified heptamethyltrisiloxane, sodium or ammonium salts of nonyl phenol ethoxyl sulfonic acid, sodium lauryl sulfate, sodium 2-ethylhexyl sulfate and sodium dioctylsulfo succinate, and ionic salts of 2-acrylamido-2-methyl propanesulfonic acid, N-vinyl caprolactam, caprolactone acrylate, N-vinyl pyrrolidone, and sulfate and acrylic monomers, for example.

"Low HLB (hydrophilic-lipophilic balance) wetting agents" are a subclass of surfactants preferred in the present invention for coating plastic surfaces to decrease contact angle and wet-out time. A low HLB wetting agent of the invention can be an anionic, a cationic, a zwitterionic or a non-ionic wetting agent, the latter being preferred. HLB numbers less than or equal to 6 are preferred; wetting agents of this type, when first dried to a surface, are essentially not solubilized when exposed to an aqueous reagent, but can be applied with alcohols, for example. The wetting agent of the invention can also be a mixture of two or more wetting agents. Candidates include, C12-C20 fatty acid esters of sucrose or xylose, glycerides of sucrose, fatty acid esters of polyoxyethylene, esters of fatty alcohols and polyoxyethylene, esters of sorbitan, esters of polyoxyethylene sorbitan, alcohol-polyglycide esters, and glyceride-polyglycides, also including for example Pluronic® L121, Pluronic® L122, PEO(2) cetyl ether (Brij® 52), PEO(2) stearyl ether (Brij® 72), Sorbitol mono-oleate (Span.® 20), Sorbitol tristearate (Span® 65), PEO(200) di-oleate (Maypeg® 200) sorbitol mono-stearate, glycerol mono-stearate, sucrose esters, alkyl naphthalene sodium sulfonate (Alkanol® B), N-octadecyl-disodium sulfosuccinamate (Aerosol® 18), polyoxyalkylene fatty ester (Nonisol® 250), dimethyl octynediol (Surfynol® 102), dimethyl hexynediol and the like.

Capillary pressure or "capillary action" describes a pressure or a movement of a liquid under that pressure respectively, also termed "capillarity", and refers to the tendency of a liquid in a microfluidic channel to advance or recede in a channel so as to minimize the overall surface free energy of the liquid/channel/vapor system. For example, a liquid with a low surface tension will advance to "wet out" a channel made from a material with a high surface energy such as glass. When injected in a microfluidic channel, liquids displaying a concave meniscus will tend to advance in the channel, and liquids displaying a convex meniscus will tend to recede. Thus capillarity is a vectored force resulting in wetting and passive flow of an aqueous liquid in a hydrophilic microfluidic channel.

"Wetout" time: refers to a measurement of the time required for a liquid to advance a standardized length in a microfluidic channel of a given geometry and surface characteristics (generally in mm/s). "Wetout" rate refers to an instantaneous rate of advance of a liquid front in a microfluidic channel in units of volume per unit time (µL/µsec) and can be modulated by surface treatments and by controlling channel geometry. Passive flow driven by downstream wetout can be used to control upstream flow velocity.

Herein, where a "means for a function" is claimed, it should be understood that the scope of the invention is not limited to the mode or modes illustrated in the drawings alone, but also encompasses all means for performing the function that are described in this specification and any equivalent means.

Means for Fabrication: Fabrication methods include laser stenciling, lamination, embossing, stamping, injection molding, masking, etching, photocatalyzed stereolithography, soft lithography, and so forth, or any combination of the above. Each cartridge can be formed of a pair of members or layers glued or fused together, or of a plurality of layers glued or fused together. The term "layer" refers to any of one or more generally planar solid substrate members or glue layers comprising a cartridge; "layers" also includes individual sheets, roll stock, and any molded body members formed as generally planar members. Layers may be joined with pressure sensitive adhesive (PSA) or thermal adhesive. Alternatively, they may be fused under pressure with heat, solvent, or by ultrasonic welding. The number of layers in the device will be dependent on the required functionalities and the fabrication process is chosen.

Plastic is a preferred material for building microfluidic devices of the present invention. Plastics which may be used include olefins, cyclic polyolefins, cyclic olefin copolymers, polyesters, polyethylene terephthalate, polybutylene terephthalate, polystyrenes, polycarbonates, polypropylene, polyethylene, polyurethane, polyether sulfone, polyvinyl chloride, polyvinyl acetate, polyamides, polyimides, polyacrylate, polymethylmethacrylate (PMMA), polytetrafluoroethylenes, polydimethylsiloxane (PDMS), polysilane, cellulose triacetate, thermoplastics in general, and so forth. Composites and copolymers are also frequently used. The knowledge to select plastics or other solid substrates and conventional adhesives is widely known in related arts.

"Conventional" is a term designating that which is known in the prior art to which this invention relates.

"About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit. For example, in various embodiments the foregoing terms refer to a quantity within 20%, 10%, 5%, 1% or 0.1% of the value which follows the term.

Unless the context requires otherwise, throughout the specification and claims which follow, the word "comprise" and variations thereof, such as, "comprises" and "comprising" are to be construed in an open, inclusive sense—that is as "including, but not limited to".

2. Features and Methods of Use for Microfluidic Cartridges and Devices for Serum Separation Exemplary embodiments of the invention can be better understood in reference to the attached figures. However, it is to be understood that the illustrated embodiments do not limit the scope of the invention and certain non-illustrated embodiments are also included.

FIG. 1 is a schematic view of the device 110 illustrating the operation of a first embodiment of the invention. As shown in FIG. 1, a microfluidic device 110 comprises a microfluidic channel 120 having a first end 122 and a second end 124. As illustrated, device 110 is in the form of a cartridge, however, the form of device 110 is not essential to the present invention and persons of ordinary skill in the art can readily select a suitable form for a given application. The microfluidic devices of the present invention, such as device 110, may be constructed from a material, such as plastic, mylar or latex, using a method such as injection molding or lamination.

As further shown in FIG. 1, device 110 comprises a sample inlet 130 fluidly connected to first end 122 of microfluidic channel 120 for receiving a liquid sample and a composite membrane 140 interposed between sample inlet 130 and first end 122 of microfluidic channel 120. As used herein, the term "membrane" refers to any planar material with a Z-dimension, including filters, which are porous membranes. Composite membrane 140 is capable of providing a matrix to hold a blood sample in place and, importantly, promoting coagulation of the blood sample. Composite membrane 140 is also capable of selectively retaining the clotted components of the blood sample and other selected particles, such as white blood cells, red blood cells, polymeric beads, such as polystyrene or latex beads with sizes from 1-100 μm, and bacteria cells, such as E. coli, from the liquid sample. Composite membrane 140 may comprise a plurality of filters or membranes or a single filter or membrane comprising a plurality of different fibers types. An optional finger pump 150 having a vent hole 152 is fluidly connected to the second end 124 of microfluidic channel 120.

During operation, a liquid blood sample is placed into sample inlet 130 (as shown in FIG. 1) whereupon the liquid blood is absorbed by membrane 140, which promotes the coagulation of the blood sample. Finger pump 150 is depressed, either manually by a user or mechanically by an external device, vent hole 152 is substantially sealed, such as by covering vent hole 152, and finger pump 150 is subsequently released. During depression of finger pump 150, vent hole 152 remains uncovered so that air in finger pump 150 may be expelled through vent hole 152. Upon release of finger pump 150, a negative fluid pressure is created in microfluidic channel 120 and a liquid serum sample is drawn through membrane 140 into, and through, microfluidic channel 120 into the sample collection well 170. In contrast, the clotted constituents as well as particles of the sample are retained by composite membrane 140 and do no enter sample collection well 170. In various embodiments, the negative pressure is provided by means other than the finger pump (e.g., an associated pneumatic instrument or other means) or the fluid moves under force of gravity.

FIGS. 2A-B depict cross-sectional views of alternative embodiments of composite membrane 140. As shown in FIG. 2A, the composite membrane may comprise two membranes, membranes 142 and 144. Membranes 142 and 144 may comprise the same or different materials. In one embodiment, the membrane 142 comprises a material that activates blood coagulation, such as glass fibers. In one embodiment, the second membrane 144 may be selected to provide particle-separation functions. In this embodiment, membrane 144 may comprise a filter with a pore size of around 1-2 μm in order to selectively remove red blood cells and white blood cells from the liquid sample. Such membranes may include, but are not limited to, asymmetric and non-asymmetric membranes comprising polysulfone (manufactured by PALL, Inc.). The two or more membranes may be stacked one on top of the other in device 110.

In operation, a blood sample is placed in sample inlet 130. When a drop of whole blood is applied to the device 110, the blood sample is drawn into membrane 142, which causes the blood to clot. Under negative pressure, the clotted sample is further drawn into second membrane 144, which retains the clotted and particulate matter while the liquid serum sample passes through the membrane into voids 182 and 184. The volume of voids 182 and 184 is sufficiently small such that the separated serum sample moves by capillary flow into the first end 122 of the microfluidic channel.

An alternative embodiment of the composite filter is shown in FIG. 2B. As depicted, composite filter 146 comprises a single membrane comprising a plurality of different fiber types, at least one of which promotes the coagulation of unclotted blood. Fibers selected for the composite filter medium include, but are not limited to, cotton linter fibers, glass microfibers, polyester (PET) staple fibers, and lower melting polyester binder fibers. Polyester staple fibers of about 1.5 denier (wherein "denier" is a term of art that refers to a unit that describes the thickness and length of a fiber) and about 0.25-in length may be the backbone of the filter to provide the gross structure of the membrane. Optionally, cotton linter fibers may be used to provide a readily wettable capillary network to passively draw the blood through the filter. Glass microfibers of about 0.40 µm mean fiber diameter may produce the fine pore structure needed for cell and particle separation. Fibers may be joined by woven or nonwoven means. Nonwoven filters may be constructed by wetlaid, spunbonded, or meltblown means. To increase strength, polyester binder fibers may optionally be added to the composite membrane.

As an alternative embodiment of the present invention, the composite membranes of FIGS. 2A-B may further contain one or more accelerators of blood coagulation. Blood coagulation activators known in the art include, but are not limited to, thrombin, snake venoms, such as Russells viper venom, platelet activating factor (PAF or ß-Acetyl-y-O-alkyl-L-∂-phosphatidylcholine), collagen, materials bearing multiple negative charges on their surfaces, such as borosilicate flakes or hallow beads, and aluminum-silicate mineral clays, such as kaolin.

Figure 3:
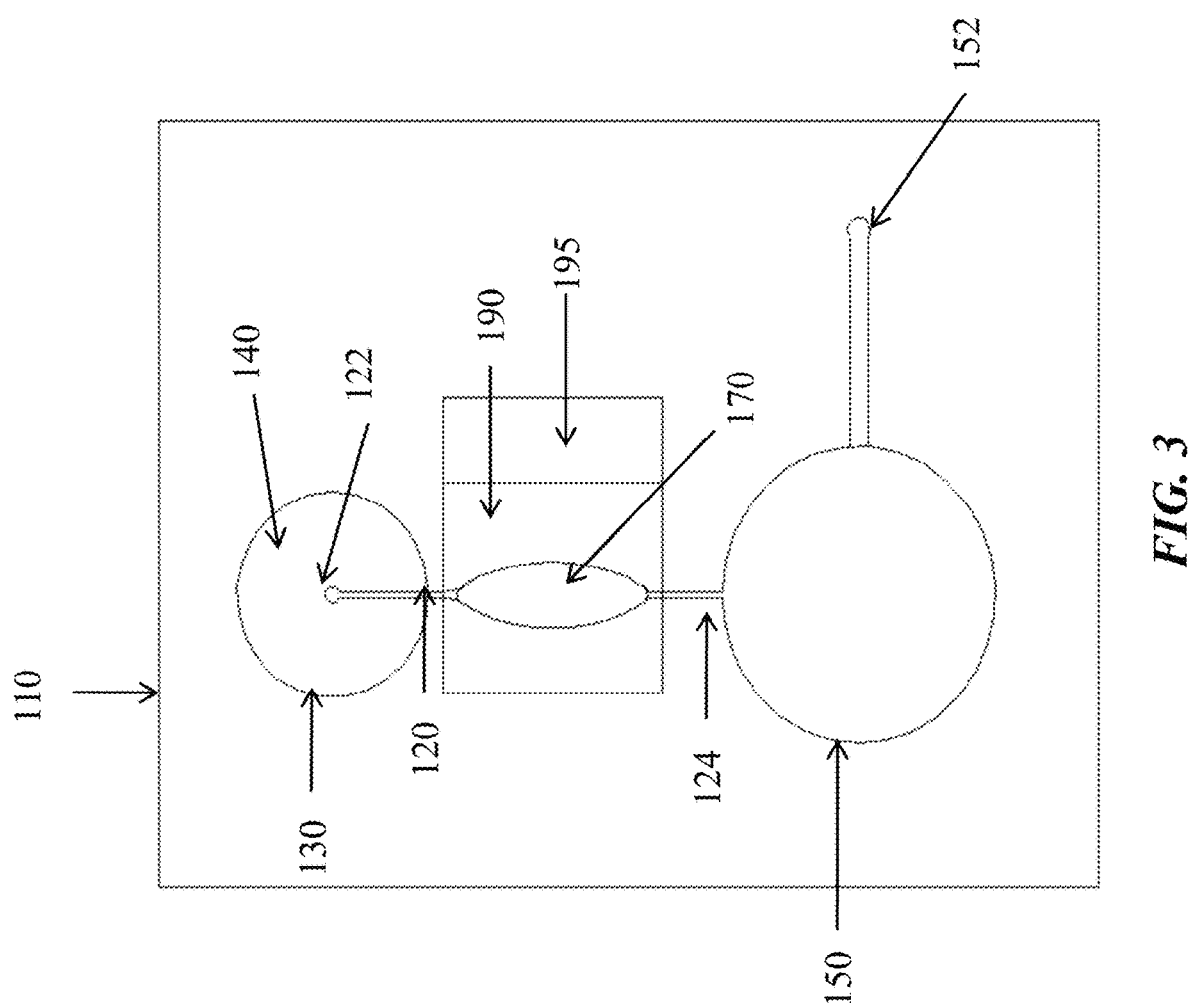
FIG. 3 is a schematic view illustrating the operation of a fourth embodiment of a microfluidic device in accordance with aspects of the present invention.

FIG. 3 is a schematic view of the device 110 illustrating the operation of one embodiment of the invention. Sample collection well 170 may be sealed with adhesive membrane 190. During operation, device 110 is supplied with sample collection well 170 sealed from the environment by adhesive membrane 190. In one embodiment of the present invention, adhesive membrane 190 is a pressure sensitive, removable tape. A liquid blood sample is placed into sample inlet 130 whereupon the liquid blood is absorbed by filter 140, which promotes the coagulation of the blood sample. Finger pump 150 is depressed, either manually by a user or mechanically by an external device, vent hole 152 is substantially sealed, such as by covering vent hole 152, and finger pump 150 is then released. During depression of finger pump 150, vent hole 152 remains uncovered so that air in finger pump 150 may be expelled through vent hole 152. Upon release of finger pump 150, a negative fluid pressure is created in microfluidic channel 120 and a liquid serum sample is drawn through membrane 140 into, and through, microfluidic channel 120 into the sample collection well 170. Adhesive membrane 190 is removed from device 110 by user manipulation of tab 195 to enable removal of a separated serum sample for further analysis. As noted above, the finger pump is not a required feature of all embodiments and fluid movement may be initiated and/or maintained by other means.

Methods for separation of serum from whole blood samples by use of the microfluidic devices are also provided. For example, in some embodiments, such methods comprise introducing the blood sample into the sample inlet of any of the disclosed microfluidic devices and contacting the blood sample with the composite membrane therein. The separated serum may then be isolated by the user and employed in further analyses, for example cross-matching analyses by contacting the isolated serum with a blood sample (e.g., a recipient blood sample) and observing the presence or absence of an agglutination reaction.

3. Features and Methods of Use for Microfluidic Cartridges and Devices for Blood Cross-Match Analysis Embodiments of the microfluidic devices of the present invention are planar, disposable cartridges that are generally credit card-sized. Most on-cartridge fluid handling and structural elements have internal dimensions ranging in size from less than 100 µm to a few mm in size and are designed to handle fluid volumes from a few microliters to a milliliter or two.

Figure 4:
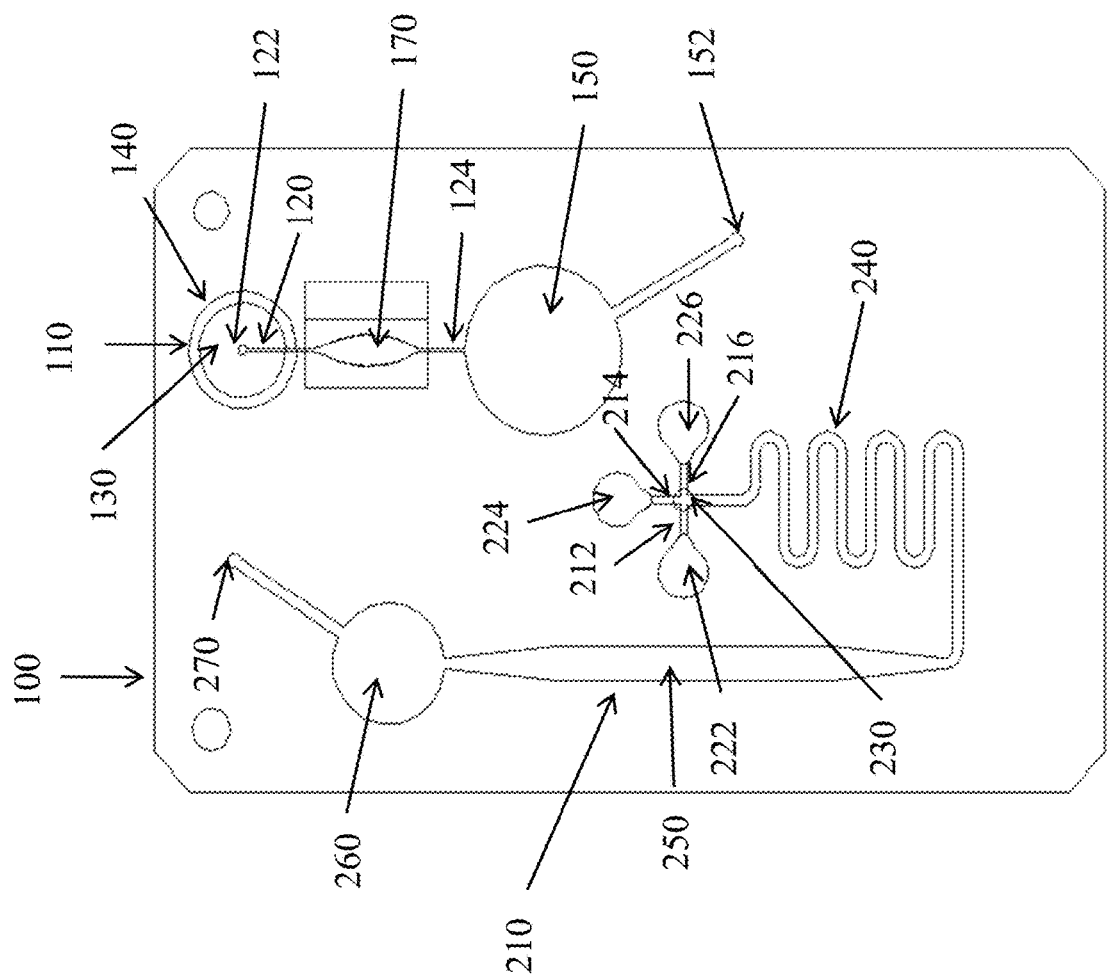
FIG. 4 is a schematic view of representative microfluidic assay circuits of the present invention.

FIG. 4 is a schematic view of a microfluidic device 100 illustrating the operation of another embodiment of the invention. As illustrated, device 100 is in the form of a cartridge, however, the form of device 100 is not essential to the present invention and persons of ordinary skill in the art can readily select a suitable form for a given application. The microfluidic devices of the present invention, such as device 100, may be constructed from a material, such as transparent plastic, mylar or latex, using a method such as injection molding or lamination.

As shown in FIG. 4, the microfluidic device 100 comprises a fluid subcircuit 110 for serum separation. Subcircuit 110 comprises a microfluidic channel 120 having a first end 122 and a second end 124. Fluid subcircuit 110 further comprises a sample inlet 130 fluidly connected to first end 122 of microfluidic channel 120 for receiving a liquid sample and a composite membrane 140 interposed between sample inlet 130 and first end 122 of microfluidic channel 120. As used herein, the term "membrane" refers to any planar material with a Z-dimension, including filters, which are porous membranes. Composite membrane 140 is capable of providing a matrix to hold a blood sample in place and, importantly, promoting coagulation of the blood sample. Composite membrane 140 is also capable of selectively retaining the clotted components of the blood sample and other selected particles, such as white blood cells, red blood cells, polymeric beads, such as polystyrene or latex beads with sizes from 1-100 µm, and bacteria cells, such as E. coli, from the liquid sample. Composite membrane 140 may be comprised of a plurality of filters or membranes or a single filter or membrane comprised of a plurality of different fibers types. A finger pump 150 having a vent hole 152 is fluidly connected to the second end 124 of microfluidic channel 120. Although illustrated with a finger pump, the finger pump is not a required feature of all embodiments and fluid movement may be initiated and/or maintained by other means.

During operation, a liquid blood sample is placed into sample inlet 130 (as shown in FIG. 4) whereupon the liquid blood is absorbed by membrane 140, which promotes the coagulation of the blood sample. Finger pump 150 is depressed, either manually by a user or mechanically by an external device, vent hole 152 is substantially sealed, such as by covering vent hole 152, and finger pump 150 is subsequently released. During depression of finger pump 150, vent hole 152 remains uncovered so that air in finger pump 150 may be expelled through vent hold 152. Upon release of finger pump 150, a negative air pressure is created in microfluidic channel 120 and a liquid serum sample is drawn through membrane 140 into, and through, microfluidic channel 120 into the sample collection well 170. In contrast, the clotted constituents of the sample are retained by composite membrane 140 and do no enter sample collection well 170.

Separated serum is to be removed manually by the user for further cross-match analysis as described below.

The cartridge of body member 100 further comprises a mixing subcircuit for the mixing of solutes between two or more liquid samples. As exemplified by the microfluidic device of FIG. 4, three intake channels 212, 214, and 216, generally with inlet wells 222, 224, and 226, are joined at a staging union 230. A liquid sample is introduced into a first inlet well and another sample or reagent liquid is introduced into a second inlet well. Optionally, a third liquid sample is introduced into a third well. One sample or reagent will include a particulate suspension of red blood cells. A second sample or reagent will include separated serum. A third, optional, sample or reagent may include a diluent, as described in greater detail below.

The microfluidic device includes micro-passive valves interposed between the intake channels 212, 214, and 216 and the staging union 230 and are configured to form a dual fluid stop. The fluid stops illustrate the general principal that an aqueous liquid will not cross a surface energy barrier without an additional force. Thus a meniscus forms where the channel geometry expands sharply and or a hydrophobic barrier surface is formed. When energy is provided, for example as a suction pulse applied downstream by finger pump 260 or other means to start the assay, all fluids will simultaneously cross the micro-passive valves and enter the common serpentine mixing channel 240. Fluids flow into serpentine mixing channel 240 by capillary action and solutes in the fluids mix together by diffusion as the liquids pass through the serpentine mixing channel. The serpentine turns of the mixing channel increase the overall length of the mixing channel, and thus the distance travelled by the liquids. Importantly, increasing the time that the liquids reside in the mixing channel through the serpentine configuration also increases the time for solutes in the liquid streams to mix by diffusion. When the particulate suspension of red blood cells is contacted with serum in the second sample, antibodies present in the second sample will cause an agglutination reaction to occur if there is no cross-match between the two samples, demonstrating they are not compatible for blood transfusion. In contrast, no agglutination reaction occurs if the first and second samples are compatible for blood transfusion. Agglutination reactions are observed by the user by the appearance of dynamically moving particle aggregates or "clumps" in the serpentine mixer 240 and the downstream channel 250 of the microfluidic device. The length of the serpentine channel is selected such that the time the flowing liquids reside in the serpentine channel is sufficient for the liquids to mix and an agglutination reaction to occur if there is no cross-match. A length which allows for sufficient mixing to enable an agglutination reaction is referred to as the "critical length."

The bottom surfaces of the inlet wells 222, 224, 226, intake channels 212, 214, 216, serpentine mixer 240, and tailpipe 250 may be coated with a surfactant to make the surfaces hydrophilic and promote the capillary flow of liquid sample through the microfluidic circuit. Agglutination reactions may be observed by the user through visual detection of moving particle aggregates or "clumps" dynamically passing through the serpentine mixer 240 and into the downstream channel 250. The downstream channel is configured such that it has a greater width than the width of the mixing channel. Due to the greater width of the downstream channel which increases the cross-sectional volume of the channel thereby reduces the velocity of the liquid front, however the flow rate of the liquid streams in the mixing channel remain the same, thereby increasing the amount of sample to be mixed in the channel.

In an alternative embodiment of the microfluidic devices of the present invention cartridge body member 100, has two intake channels 212 and 216, generally with inlet wells 222 and 226, joined at a staging union 230. A liquid sample containing a particulate suspension of red blood cells is introduced into channel 212; a second liquid sample containing separated serum is introduced into channel 216. In this embodiment of the invention, dilution of the particulate blood sample may be performed off-cartridge, prior to loading of the blood sample into inlet well 222 of the microfluidic device of FIG. 4. A red blood cell diluent may be included to achieve any of the following advantages: reduction of the concentration of agglutinins in the donor blood that may participate in an auto-immune reaction with the donor red bloods cells and induce hemolysis or agglutination as a side-reaction; reduction of the Zeta potential (negative surface charge) on the donor red blood cells, which inhibits cellular aggregation; reduction in the density of red blood cells in the detection window, such that aggregates of cells are more easily viewed; or prevention of complement-mediated steric hindrance of antibody-antigen binding that might contribute to a false negative reaction (e.g., a cross-match). Exemplary diluents include but are not limited to isotonic saline solutions that may or may not include EDTA to prevent clotting of donor blood prior to cross-match analysis. When the particulate blood sample and diluent are contacted with serum in the second sample, antibodies present in the second sample will cause an agglutination reaction to occur if there is no cross-match between the red blood cell and serum samples, indicating and they are not compatible for a blood transfusion. In contrast, no agglutination reaction will occur if the particulate and serum samples are compatible for a blood transfusion. Agglutination reactions are observed by the user by the appearance of dynamically moving particle aggregates or "clumps" in the serpentine mixer 240 and the downstream channel 250.

Figure 5:
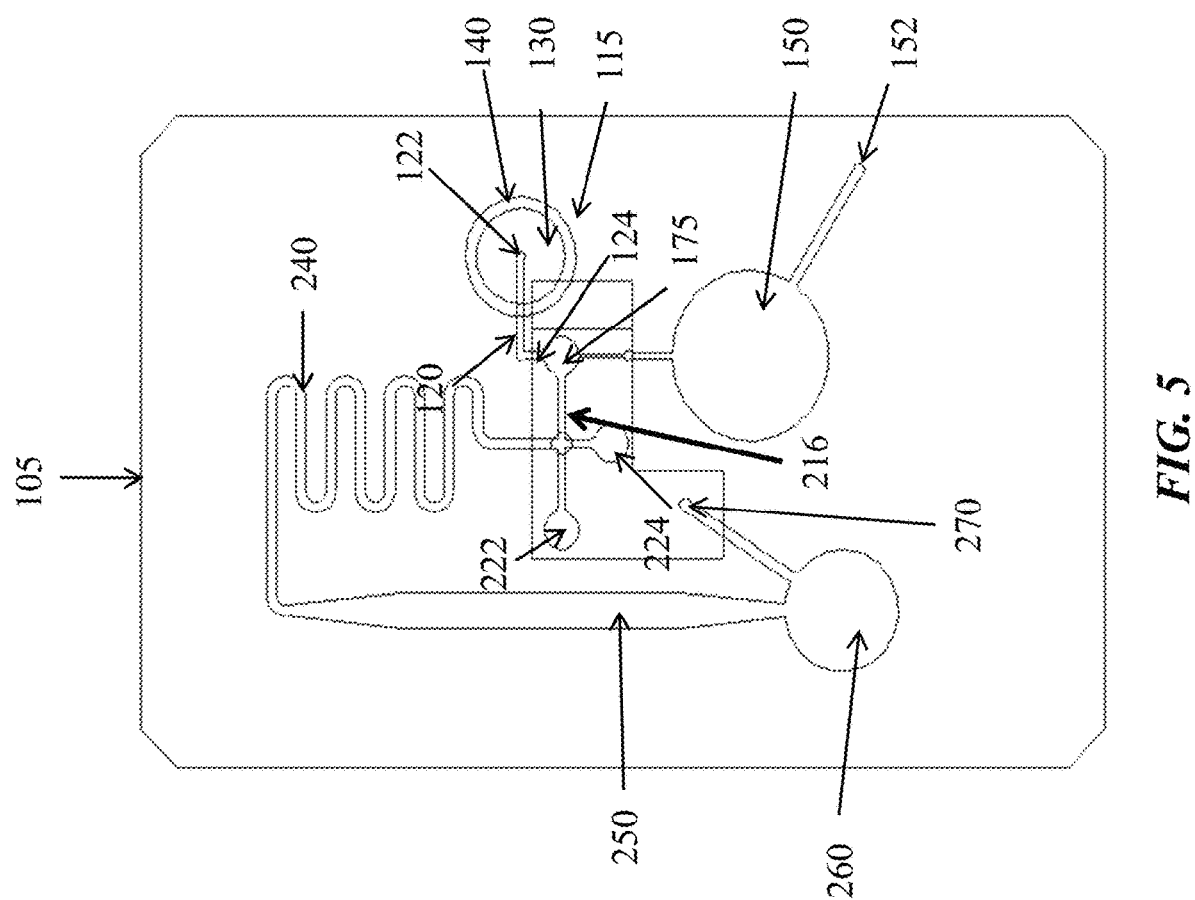
FIG. 5 is a schematic of a second embodiment of the microfluidic assay circuits of the present invention.

Another alternative embodiment of the microfluidic devices of the present invention is shown in FIG. 5. In this embodiment, microfluidic device 105 comprises a fluid subcircuit 115 for serum separation that is fluidly connected to intake channel 216. Serum separation is performed as described above; however, in this embodiment of the invention, the serum collection chamber 175 functions as sample inlet well 226 of the embodiment of FIG. 4. The principles of operating microfluidic device 105 of this embodiment of the invention are similar to those of microfluidic device 100, except that operation of microfluidic device 105 does not require that the user manually apply a serum sample to a sample inlet well.

Methods for use of any of the foregoing microfluidic devices in cross-matching of two different blood samples, such as cross match of a donor blood sample and a recipient blood sample, are also provided. For example, the methods may be for performing a cross match of a donor blood sample and a recipient blood sample. In one of these embodiments, the method comprises:

a) contacting the donor blood sample with the composite membrane of any of the foregoing microfluidic devices;

b) isolating serum from the donor blood sample;

c) contacting the isolated serum with the recipient blood sample; and d) observing the presence or absence of an agglutination reaction.

Advantageously, certain embodiments of the methods are performed using microfluidic devices in which a fluid subcircuit for serum separation is fluidly connected to a sample inlet and mixing channel (e.g., as described with respect to FIG. 5). In embodiments of these methods, serum separation is performed, and the separated serum is contacted with a whole blood sample on the same microfluidic device. For example, in some embodiments the cross matching methods comprise:

a) introducing a donor blood sample into a serum separation subcircuit of a microfluidic device having fluidly connected serum separation subcircuits and solute mixing subcircuits (e.g., as described above in reference to FIG. 5) and contacting the donor blood sample with a composite membrane in the serum separation subcircuit to separate donor serum from the donor blood sample;

b) contacting the donor serum with a recipient blood sample in a mixing channel of the solute mixing subcircuit; and c) observing the presence or absence of an agglutination reaction.

EXAMPLES

Example 1: Assessment of Glass Fiber Filters in Promoting Blood Coagulation

This example demonstrates that glass fiber filters promote blood coagulation on a microfluidic device.

Various borosilicate glass fiber filters as set forth in Table 1 were stacked with the Pall Vivid GR membrane and laminated into "cartridges" (i.e., into a microfluidic device) using standard construction methods known in the art. For testing, 100 µL of fresh, whole blood was applied to the filter and allowed to clot for up to 15 minutes. Liquid sample was pulled by vacuum into a collection chamber. Performance of the filters was evaluated based on the volume of serum obtained in one minute and on the color of the serum. As shown in Table I, several of the glass fiber filters tested enabled on-card serum separation. Pink serum indicates that some degree of hemolysis has occurred. These results indicate that serum separation can, surprisingly, be achieved on-card (i.e., within a microfluidic device) by incorporation of a glass fiber filter into the design of the device. Interestingly, not all glass fiber filters displayed identical properties in this assessment. The function of the Porex glass fiber filter was superior to the others in that it did not promote hemolysis, but rather generated a clear serum sample. Pore size or filter thickness of the glass fiber filters tested varied, but no correlation was observed with performance.

Thus, this unique composite filter design, which introduces a borosilicate glass fiber filter, displays superior functionality over prior art filtering devices. While the prior art blood filters are limited to performing particle separation, the composite filters of the present invention can further promote blood coagulation, thereby removing inhibitory clotting factors and providing serum for further diagnostic analysis.

TABLE 1

Borosilicate glass fiber filters tested in serum separation

| Brand (Glass fiber) | Grade | Pores (microns) | Thickness (microns) | Volume (µL) | Color |
|---|---|---|---|---|---|
| Porex | D | 2.7 | 640 | 20 | Clear |
| Pall | A/D | 3.1 | 580-740 | 20 | Pink |
| Whatman | GF/D | 2.7 | 675 | 20 | Pink |

TABLE 1-continued

Borosilicate glass fiber filters tested in serum separation

| Brand (Glass fiber) | Grade | Pores (microns) | Thickness (microns) | Volume (µL) | Color |
|---|---|---|---|---|---|
| Macherey Nagel | MN 85/90 BF | 0.5 | 400 | 20 | Pink |

Example 2: Design of a Microfluidic Subcircuit for Serum Separation

This example demonstrates serum separation by a microfluidic device incorporating a glass fiber, composite filter.

A microfluidic subcircuit with a collection chamber and a port was designed to separate serum from a whole blood sample. Fresh, whole finger-stick collected blood (approximately 200 µL) was applied to a composite filter as described above and allowed to clot. In operation, the user's index finger compresses a finger pump, while a second finger covers the vent holes. The vacuum generated when the index finger is removed pulls the sample through the filters into the collection chamber. The filtered sample was collected using a mechanical pipettor with a disposable tip. The recovered material was characterized as serum by measurement of the residual fibrinogen content. Plasma contains fibrinogen, while serum is depleted of this protein due to activation of the clotting cascade, during which fibrinogen is converted into insoluble fibrin to create the blood clot. The blood clot is retained in the composite filter, while the liquid serum passes through the filter and into the collection chamber.

Figure 6:
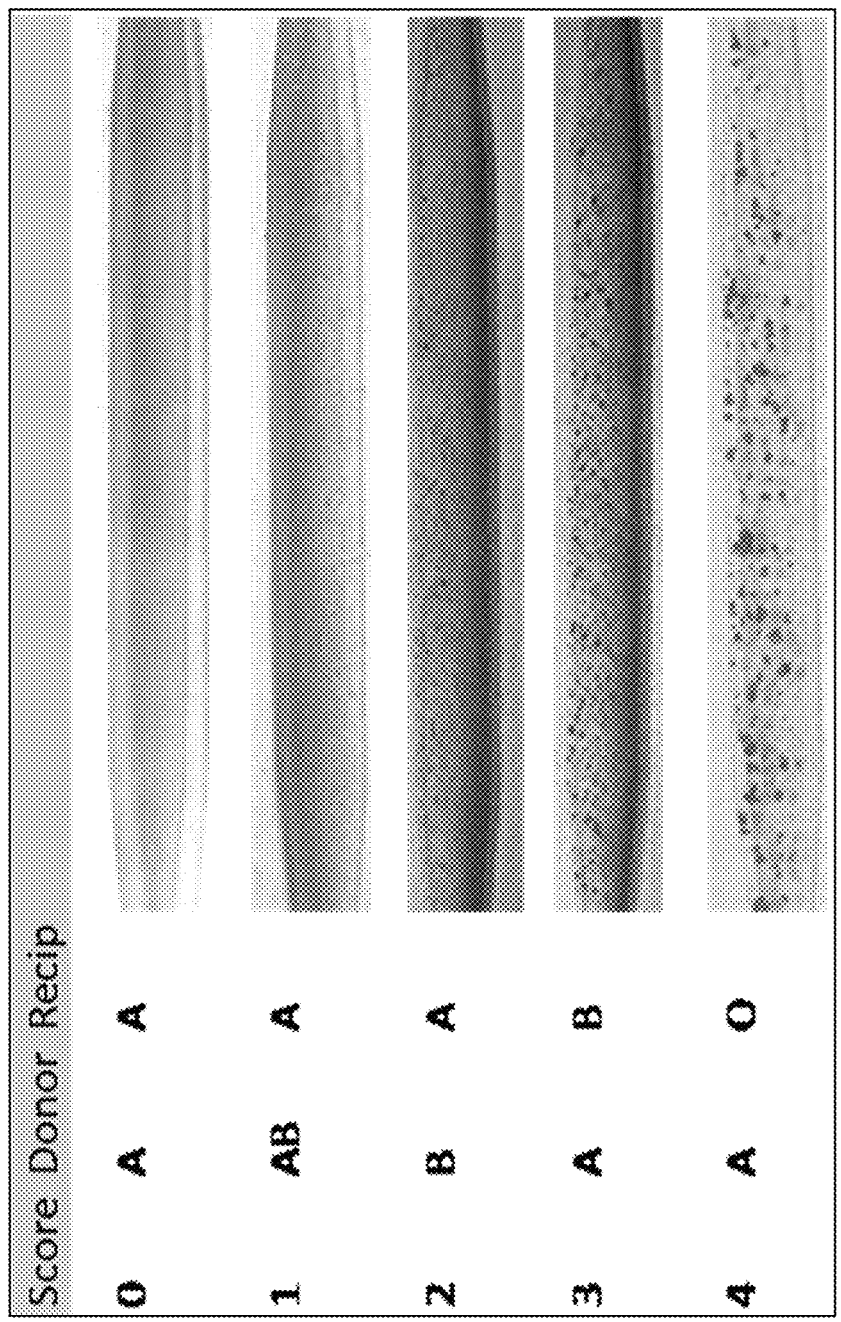
FIG. 6 shows results of cross-match reactions between different donors and recipients using a microfluidic device of the present invention.

A fibrinogen ELISA kit (manufactured by Alpco Diagnostics, Salem, N.H.) was used to measure fibrinogen content of the samples. Samples recovered from the serum separation subcircuit were compared to serum generated by the conventional protocol of blood clotting and centrifugation in vacucontainers. Plasma collected in vacutainers containing sodium citrate as an anticoagulant was also assayed. Four different plasma samples were found to contain from 2.9 to 4.2 mg/mL fibrinogen, while serum samples generated by centrifugation were found to be mostly depleted of fibrinogen, containing from 0 to 300 ng/mL fibrinogen (approximately 10,000 fold less than plasma). Surprisingly, as shown in FIG. 6, the amount of fibrinogen detected in each of the eleven samples of material obtained from the serum separation subcircuit was also negligible (from 0 to 3000 ng/mL fibrinogen). These results demonstrate the successful design of a serum separation subcircuit into a microfluidic device through use of a glass fiber, composite filter. The microfluidic devices disclosed herein offer significant advantages over conventional serum separation protocols, which require large, heavy, and costly laboratory equipment to practice.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Patent Application Nos. 61/820,576; 61/820,585 and 61/820,579; each filed May 7, 2013, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microfluidic device comprising:
   a fluid separation subcircuit including a membrane capable of activating blood coagulation; and
   a solute mixing subcircuit fluidically coupled to the fluid separation subcircuit, the solute mixing subcircuit including:
   a first intake channel for conveying a first fluid;
   a second intake channel for conveying a second fluid;
   a third intake channel for conveying a third fluid;
   a staging union that is fluidically coupled to the first intake channel, the second intake channel, and the third intake channel;
   a first micro-passive valve interposed between the first intake channel and the staging union;
   a second micro-passive valve interposed between the second intake channel and the staging union;
   a third micro-passive valve interposed between the third intake channel and the staging union;
   a mixing channel having a first end and a second end, wherein the staging union is fluidically coupled to the first end of the mixing channel, and wherein the first, second, and third micro-passive valves are configured to simultaneously release the first, second, and third fluids through the staging union into the mixing channel; and
   a pump for controlling fluid flow across the first, second, and third micro-passive valves, wherein the pump is fluidically coupled to the second end of the mixing channel.

2. The microfluidic device of claim 1 wherein the mixing channel is a serpentine mixing channel.

3. The microfluidic device of claim 1 wherein the mixing channel has a first width and the second end of the mixing channel is fluidically coupled to a downstream channel having a second width that is greater than the first width.

4. The microfluidic device of claim 3 wherein the pump is fluidically coupled to the downstream channel and is fluidically coupled to the second end of the mixing channel by the downstream channel.

5. The microfluidic device of claim 3 wherein a surface of the downstream channel is coated in a surfactant.

6. The microfluidic device of claim 3 wherein a surface of the downstream channel is hydrophilic.

7. The microfluidic device of claim 1 wherein surfaces of the first, second, and third intake channels are coated in a surfactant.

8. The microfluidic device of claim 1 wherein surfaces of the first, second, and third intake channels are hydrophilic.

9. The microfluidic device of claim 1 wherein a surface of the mixing channel is coated in a surfactant.

10. The microfluidic device of claim 1 wherein a surface of the mixing channel is hydrophilic.

11. The microfluidic device of claim 1 wherein the solute mixing subcircuit further includes a vent.

12. The microfluidic device of claim 1 wherein the first fluid includes a particulate suspension of red blood cells, the second fluid includes separated serum, and the third fluid includes a diluent.

13. The microfluidic device of claim 12 wherein the diluent includes an isotonic saline solution.

14. The microfluidic device of claim 12 wherein the diluent includes EDTA.

15. The microfluidic device of claim 12 wherein the fluid separation subcircuit is fluidically coupled to the second intake channel.

16. The microfluidic device of claim 12 wherein the mixing channel has a length sufficient for an agglutination reaction between the particulate suspension of red blood cells and the separated serum flowing through the mixing channel to occur.

* * * * *